United States Patent
Pundlik et al.

(10) Patent No.: US 11,937,877 B2
(45) Date of Patent: Mar. 26, 2024

(54) MEASURING DARK ADAPTATION

(71) Applicant: The Schepens Eye Research Institute, Inc., Boston, MA (US)

(72) Inventors: Shrinivas Pundlik, Arlington, MA (US); Gang Luo, Lexington, MA (US)

(73) Assignee: The Schepens Eye Research Institute, Inc., Boston, MA (US)

(*) Notice: Subject to any disclaimer, the term of this patent is extended or adjusted under 35 U.S.C. 154(b) by 832 days.

(21) Appl. No.: 16/971,975

(22) PCT Filed: Feb. 22, 2019

(86) PCT No.: PCT/US2019/019230
§ 371 (c)(1),
(2) Date: Aug. 21, 2020

(87) PCT Pub. No.: WO2019/165263
PCT Pub. Date: Aug. 29, 2019

(65) Prior Publication Data
US 2020/0397281 A1    Dec. 24, 2020

Related U.S. Application Data

(60) Provisional application No. 62/633,976, filed on Feb. 22, 2018.

(51) Int. Cl.
*A61B 3/06*    (2006.01)
*A61B 3/00*    (2006.01)
(Continued)

(52) U.S. Cl.
CPC .............. *A61B 3/063* (2013.01); *A61B 3/005* (2013.01); *A61B 3/0058* (2013.01); *G02B 27/017* (2013.01); *G06F 3/013* (2013.01)

(58) Field of Classification Search
CPC ....... A61B 3/063; A61B 3/005; A61B 3/0058; A61B 5/6898; A61B 5/6803; G02B 27/017; G06F 3/013
See application file for complete search history.

(56) References Cited

U.S. PATENT DOCUMENTS 10,251,542 B1 *   4/2019   Arnow ..................... A61B 3/02
2009/0220415 A1    9/2009   Shachaf et al.
(Continued)

FOREIGN PATENT DOCUMENTS

EP           0361766 A1 *   4/1990
WO      2001/06914 A1    2/2001
(Continued)

OTHER PUBLICATIONS

International Search Report and Written Opinion of International Application No. PCT/US2019/019230 dated May 15, 2019, 11 pages.

*Primary Examiner* — Wyatt A Stoffa
*Assistant Examiner* — Ray Alexander Dean
(74) *Attorney, Agent, or Firm* — Quarles & Brady LLP

(57) ABSTRACT

Methods, systems, and devices are provided for measuring dark adaptation of one or both eyes of a patient, and more particularly, for measuring dark adaptation with a mobile device application. An exemplary method includes exposing an eye of a patient to a light source to bleach a retinal location of the eye, displaying on a mobile device a figure with a luminance and waiting until the patient communicates with the mobile device to acknowledge that the patient can see the figure, measuring and recording a level of the luminance and a time period between first displaying the figure and the patient communicating with the mobile device, continuing to display additional figures with decreasing luminance one at a time, and determining by a (Continued)

processor dark adaptation measurements of the patent based on the measured and recorded luminance and time periods.

18 Claims, 16 Drawing Sheets

(51) Int. Cl.
*G02B 27/01* (2006.01)
*G06F 3/01* (2006.01)

(56) References Cited

U.S. PATENT DOCUMENTS

| | | |
|---|---|---|
| 2010/0118379 A1 | 5/2010 | Lim |
| 2012/0212706 A1* | 8/2012 | Chou ............... A61B 3/036 |
| | | 351/246 |
| 2013/0155376 A1 | 6/2013 | Huang et al. |
| 2015/0305616 A1 | 10/2015 | Jackson et al. |
| 2016/0073877 A1 | 3/2016 | Su et al. |
| 2016/0262608 A1 | 9/2016 | Krueger |
| 2017/0135577 A1* | 5/2017 | Komogortsev ........ A61B 5/168 |
| 2018/0110409 A1* | 4/2018 | Tsapakis ............... A61B 3/024 |

FOREIGN PATENT DOCUMENTS

| | | |
|---|---|---|
| WO | 2016/179370 A1 | 11/2016 |
| WO | 2019/165263 A1 | 8/2019 |

\* cited by examiner

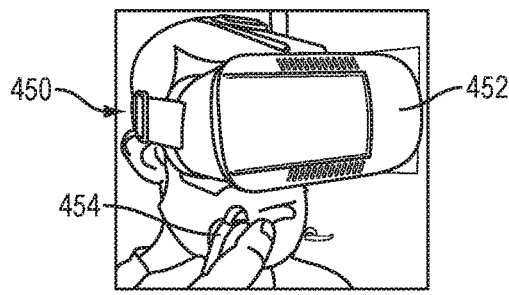
FIG. 8A
| Direct viewing mode | |
|---|---|
| Eye to screen distance | 40 cm |
| Overall display size | 17° horizontal x 30° vertical |
| Stimulus size | 0.5° |
| Stimulus eccentricity | 8° (max. allowable up to 15°) |
| Stimulus display duration | 0.3 s |
| Stimulus wavelength | 425 nm |
| Stimulus intensity range | >4 log Cd/m² |
| Minimum stimulus intensity | 1.95x10⁻⁴ Cd/m² or -3.71 log Cd/m² |
FIG. 8B
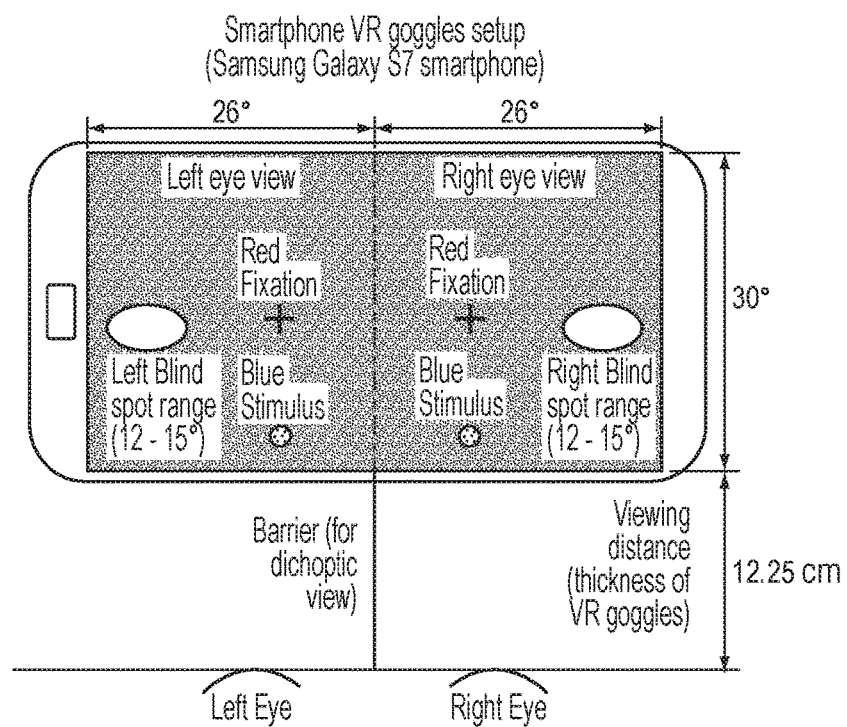
FIG. 8C

MEASURING DARK ADAPTATION

RELATED APPLICATIONS

The present application is a national stage of Application PCT/US19/19230, which claims priority to U.S. Provisional Application 62/633,976 filed on Feb. 22, 2018 and entitled "Measuring Dark Adaption." The entire contents of these applications are incorporated herein by reference in their entirety.

FIELD

The present disclosure relates generally to measuring dark adaptation in an eye, and more particularly, to a mobile device application for dark adaptation measurement.

BACKGROUND

Generally, dark adaptation (DA) is the natural process through which eyes adapt to low light intensities and/or darkness. During exposure to light, a biological visual pigment in photoreceptors of a patient's retina is bleached in response to light. When light is reduced or terminated, dark adaptation begins in the patient's retina. Dark adaptation of both rods and cones within the patient's retina requires regeneration of this visual pigment. Cones regenerate the pigment faster than rods, and cones will thus saturate early in a patient's retina during dark adaptation because cones have a lower light sensitivity as compared to rods. Rods have a higher sensitivity to light, and rods will consequently take longer to fully adapt to the change in light and reach their absolute sensitivity threshold. The transition from cone to rod mediated dark adaptation is called the rod-cone break (RCB).

The overall steps in the dark adaptation process is generally the same between people with normal eye function and people with impaired eye function, such as people with various retinal disorders. However, due to impaired rod and cone functioning, some dark adaptation characteristics may appear different in people with various retinal disorders compared to those with healthy eyes. For example, the dark adaptation process may show select characteristics that are impaired or altered in patients with some degree of retinal degeneration, such as age-related macular degeneration (AMD) or diabetic retinopathy (DR). As one example, these patients with maculopathies may have lower photoreceptor sensitivities and take longer to adapt to darkness when compared to age-matched controls with healthy eyes. These changes in the dark adaptation characteristics can be correlated with severity of the underlying condition, such as AMD.

Loss of vision is typically noticed by the patient only during later stages of various retinal disorders. Thus, visual acuity (VA) only serves as a limited functional outcome measure for detection or determining severity of various retinal disorders. On the other hand, the dark adaptation process can be affected early in the disease progression of various retinal disorders, even when the visual acuity loss is not noticeable. Because of this early identification of a potential retinal disorder, measuring dark adaptation in patients can serve as a useful functional vision measure for early detection and for monitoring the progression of various retinal disorders, such as AMD.

Clinical dark adaptometer devices are currently in use and are on the market. However, their use has been restricted because of their limited accessibility, high cost, and need for expert handling. Thus the current devices cannot be used for home monitoring or easy screening purposes.

SUMMARY

The method, systems, and devices provided herein provide solutions to problems or drawbacks associated with the current dark adaptometer devices, such as difficulty of use, expense, and lack of access to screening devices. Methods, systems, and devices are thus provided herein for measuring dark adaptation in an eye of a patient, and more particularly, for measuring dark adaptation with a mobile device application on a mobile device, such as any portable computing device. Included herein would be any computing device that is small enough to hold and operate in the hand, such as a device that is smaller than about 20 inches (such as about 5 inches, about 10 inches, about 15 inches, etc.) by about 15 inches (such as about 5 inches, about 10 inches, etc.) by about 4 inches (such as about 1 inch, about 2 inches, about 3 inches, etc.) and weighs less than about 10 pounds (such as about 1 pound, about 2 pound, about 3 pounds, etc.). Some non-limiting examples of computing devices are a mobile phone, a tablet computer, or a laptop computer. For example in one exemplary embodiment, a method for measuring dark adaptation characteristics is provided that includes exposing at least one eye of a patient to a light source to bleach a retinal location of the at least one eye and displaying to the at least one eye on a mobile device a figure with a luminance and waiting until the patient communicates with the mobile device to acknowledge that the patient can see the figure. The method also includes measuring and recording a level of the luminance and a time period between first displaying the figure and the patient communicating with the mobile device. The method further includes continuing to display additional figures with decreasing luminance one at a time until the patient communicates with the mobile device to acknowledge that the patient can see each additional figure and to measure and record each decreasing luminance and each time period between first displaying each additional figure and the patient communicating with the mobile device until either a maximum allowable time period has expired or an additional figure with a lowest possible luminance has been displayed by the mobile device and acknowledged by the patient. The method also includes determining, by a processor, dark adaptation measurements of the at least one eye based on the measured and recorded luminance and time periods.

The method can have numerous variations. For example, the method can also include, prior to exposing the eye of the patient to a light source, placing a rear surface of the mobile device facing the patient with at least one luminescent visual target thereon such that the patient can see the luminescent visual target. In another example, exposing the eye of the patient to the light source to bleach the retinal location of the eye can also include actuating a flash on the mobile device. Exposing the eye of the patient to the light source to bleach the retinal location of the eye can further include increasing brightness of a display on the mobile device. In another example, exposing the eye of the patient to the light source to bleach the retinal location of the eye can include waiting until the patient communicates with the mobile device to actuate the light source. In another embodiment, the method can include placing an eye patch over an eye of the patient that is not being measured. The method can also include incrementing luminance of a displayed figure and waiting until the patient communicates with the mobile device to acknowledge that the patient can see the displayed figure The method can also include placing the mobile device in virtual reality goggles. In another example, the method includes placing the mobile device in a mobile device viewer and placing the mobile device viewer over first and second eyes of the patient. The mobile device viewer can have only one lens over the first eye of the patient and an open space over the second eye of the patient. The mobile device viewer can be configured to exclude all external light not generated by the mobile device. The mobile device viewer can also have an opaque barrier between the first eye and the second eye of the patient. In another example, the method includes selecting an operating mode of the mobile device from one of a single eye measurement mode and a dual eye measurement mode. The dual eye measurement mode can include exposing both eyes of the patient to the light source and determining, by the processor, dark adaptation measurements of both eyes of the patient based on the measured and recorded luminance and time periods. In another example, the mobile device can be one of a mobile phone, a tablet computer, or a laptop computer. The method can also include actuating a front-facing flash on the mobile device. In another example, the method can include increasing brightness of the display on the mobile device while presenting one or more moving targets on the display. The mobile device can instruct the patient to stare at the one or more moving targets for at least 2 minutes. The method can also include waiting until the patient taps on the one or more moving targets.

In another embodiment, a method is provided for measuring dark adaptation characteristics of a patient using a mobile device that includes exposing at least one eye of the patient to a light source on the mobile device to bleach a retinal location of the at least one eye. The method also includes displaying to the at least one eye on a display of the mobile device a fixation target and a test stimulus such that the fixation target has a constant luminance and the test stimulus has a variable luminance. The method also includes instructing the patient by the mobile device to look at the fixation target with the at least one eye and waiting until the patient communicates with the mobile device to acknowledge that the patient can see the test stimulus with the at least one eye. The method further includes reducing the luminance of the test stimulus on the display of the mobile device and waiting for the patient to acknowledge that the patient can see the test stimulus with the reduced luminance. The method also includes continuing to reduce the luminance of the test stimulus on the display and waiting for the patient to acknowledge that the patient can see each reduced luminance test stimulus until either a maximum allowable time period has expired or the test stimulus with a lowest possible luminance has been displayed by the mobile device and acknowledged by the patient, and recording in a memory of the mobile device a level of the luminance of the test stimulus and a time period between first displaying the test stimulus and the patient communicating with the mobile device for each instance of displaying the test stimulus. The method also includes determining, by a processor of the mobile device, dark adaptation measurements of the at least one eye based on the measured and recorded luminance and time periods.

The method can have a variety of embodiments. For example, the method can further include instructing by the mobile device the patient to place an eye patch over an eye of the patient that is not being measured. The method can also include exposing both eyes of the patient to the light source and determining, by the processor, dark adaptation measurements of both eyes of the patient based on the measured and recorded luminance and time periods. The method can additionally include placing the mobile device in virtual reality (VR) goggles, for example, eyewear and/or a head-worn apparatus that at least partially or completely covers a user's eyes for a visual and optionally auditory experience (such as a 3-dimensional immersive experience) that can be entirely self-contained or can connect to one or more external components. In another example, the method can include placing the mobile device in a mobile device viewer and placing the mobile device viewer over first and second eyes of the patient such that the mobile device viewer has only one lens over the first eye of the patient and an open space over the second eye of the patient. In still another example, the mobile device is one of a mobile phone, a tablet computer, or a laptop computer. The method can also include monitoring fixation of the first eye based on images taken of the second eye by an imaging device of the mobile device.

In another aspect, a system for measuring dark adaptation characteristics of a patient is provided that includes a mobile device with at least one light source, at least one input device, at least one imaging device, memory, at least one processor, and a display. The display is configured to display a fixation target and a test stimulus, and the fixation target has a constant luminance while the test stimulus has a variable luminance. The processor is configured to measure luminance of the test stimulus and a time period between displaying the test stimulus and the patient acknowledging the test stimulus. The processor is also configured to determine dark adaptation measurements of at least one tested eye based on the measured and recorded luminance and time periods. The system further includes a mobile device viewer that is configured to receive the mobile device and be placed over first and second eyes of the patient. The mobile device viewer has one lens over the first eye of the patient and an open space over the second eye of the patient.

The system can have numerous variations. For example, the at least one imaging device can include a forward-facing camera on the mobile device. The at least one imaging device can include a rear-facing camera on the mobile device. The at least one light source can include a forward-facing flash on the mobile device, and the at least one light source can include a rear-facing flash on the mobile device.

In another aspect, a device for holding a mobile device for measuring dark adaptation characteristics of a patient is provided that includes a viewer configured to receive the mobile device therein and be placed over first and second eyes of the patient. The viewer has one lens that is configured to be positioned over the first eye (for example a test eye) of the patient and an open space that is configured to be positioned over the second eye (for example a fellow eye or non-testing eye) of the patient. The viewer is configured to position a display of the mobile device in front of the first and the second eyes of the patient and point a camera of the mobile device in a direction of at least one of the first and second eyes of the patient.

The device can have a variety of embodiments. For example, the viewer can be configured to point the camera of the mobile device at the second eye of the patient.

In another aspect, a method for measuring dark adaptation characteristics of a patient using VR goggles can be provided that includes exposing an at least first eye of the patient to a light source in the VR goggles to bleach a retinal location of the at least first eye. The method also includes displaying to the at least first eye on a display of the VR goggles a first fixation target and a first test stimulus. The first fixation target has a constant luminance, and the first test stimulus has a variable luminance. The method also includes instructing the patient by the VR goggles or an associated computer system to look at the first fixation target with the at least first eye and waiting until the patient communicates with the VR goggles or the associated computer system to acknowledge that the patient can see the first test stimulus with the at least first eye. The method further includes reducing the luminance of the first test stimulus on the display of the VR goggles and waiting for the patient to acknowledge that the patient can see the first test stimulus with the reduced luminance. The method also includes continuing to reduce the luminance of the first test stimulus on the display and waiting for the patient to acknowledge that the patient can see each reduced luminance first test stimulus until either a maximum allowable time period has expired or the first test stimulus with a lowest possible luminance has been displayed by the VR goggles and acknowledged by the patient. The method includes recording in a memory of the VR goggles or the associated computer system a level of the luminance of the first test stimulus and a time period between first displaying the first test stimulus and the patient communicating with the VR goggles or the associated computer system for each instance of displaying the first test stimulus. The method also includes determining, by a processor of the VR goggles or the associated computer system, dark adaptation measurements of the at least first eye based on the measured and recorded luminance and time periods.

The method can have numerous variations. For example, the method can include exposing a second eye of the patient to the light source; displaying to the second eye a second fixation target and a second test stimulus with the second fixation target having a constant luminance and the second test stimulus having a variable luminance; instructing the patient by the VR goggles to look at the second fixation target with the second eye and waiting until the patient communicates with the VR goggles or the associated computer system to acknowledge that the patient can see the second test stimulus with the second eye; reducing the luminance of the second test stimulus on the display of the VR goggles and waiting for the patient to acknowledge that the patient can see the second test stimulus with the reduced luminance; continuing to reduce the luminance of the second test stimulus on the display and waiting for the patient to acknowledge that the patient can see each reduced luminance second test stimulus until either a maximum allowable time period has expired or the second test stimulus with a lowest possible luminance has been displayed by the VR goggles and acknowledged by the patient; recording in a memory of the VR goggles or the associated computer system a level of the luminance of the second test stimulus and a time period between first displaying the second test stimulus and the patient communicating with the VR goggles or the associated computer system for each instance of displaying the second test stimulus; and determining, by the processor, dark adaptation measurements of each of the first and second eyes of the patient based on the measured and recorded luminance and time periods. In such an example, the first and second fixation targets and the first and second test stimuluses can be presented to the first and second eyes through an alternating pattern such that each of the first and second eyes can be measured simultaneously. The VR goggles can also visually isolate the first and second eyes relative to each other during measuring.

In other examples, the method can also include monitoring fixation of the at least first eye based on images taken of a second eye of the patient by an imaging device of the VR goggles. In another example, the VR goggles can include dedicated VR goggles with built-in eye-tracking functionality. In another example, the associated computer system includes at least one of a gaming console, a mobile phone, a tablet computer, a desktop computer, a device with a processor and a memory, a remote server, and a laptop computer.

BRIEF DESCRIPTION OF THE DRAWINGS

The invention will be more fully understood from the following detailed description taken in conjunction with the accompanying drawings, in which:

FIG. 8A illustrates a patient using the procedure of FIG. 7 with an exemplary mobile device, the Galaxy S7;

FIG. 8B illustrates various specifications of the exemplary mobile device of FIG. 8A;

FIG. 8C illustrates an annotated screen shot of the mobile application of FIG. 7 in use;

Figure 1:
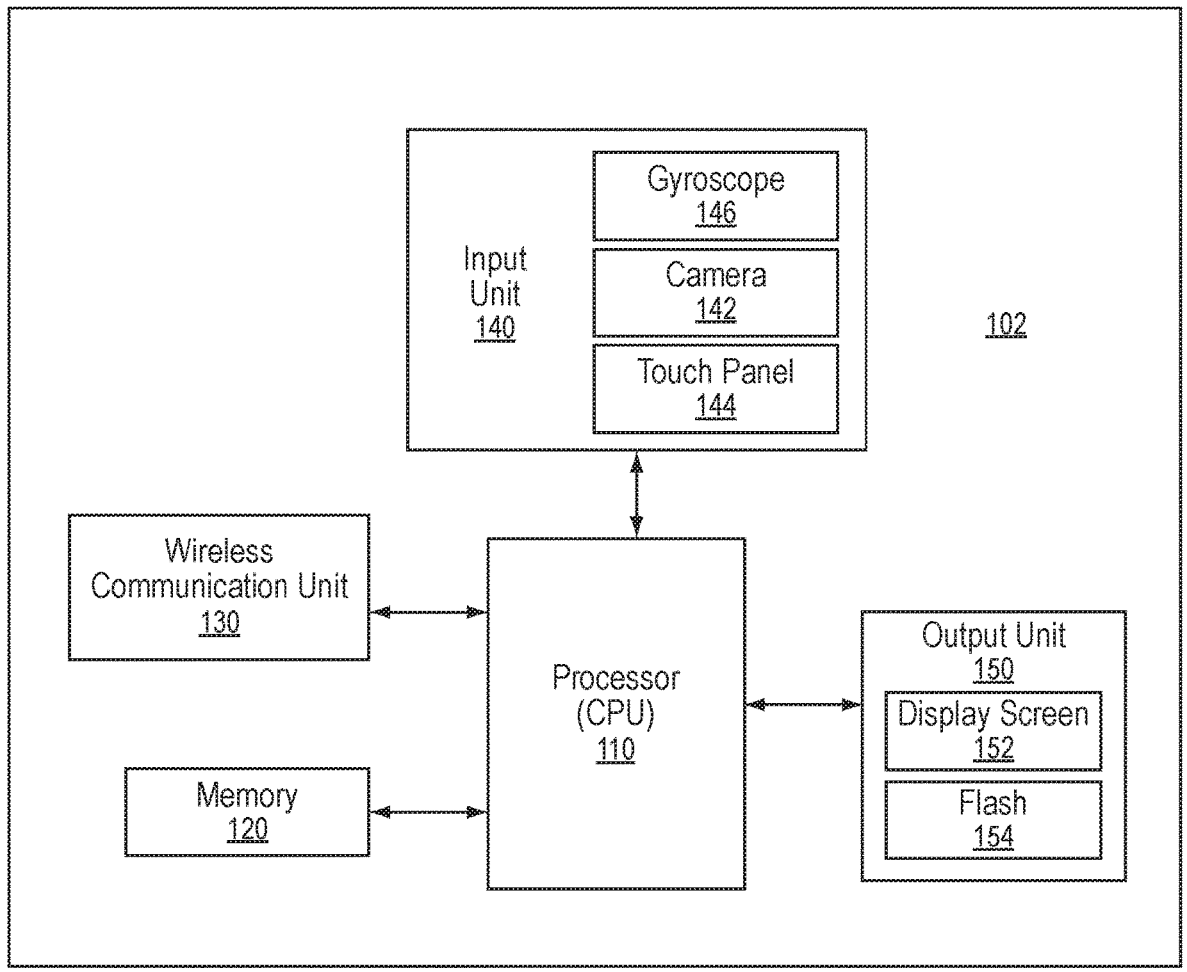
FIG. 1 illustrates an example diagrammatic view of a mobile device architecture.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

It is understood that the term "mobile device" or other similar term as used herein is inclusive of any portable computing device, such as smart phones, tablets, laptops, PDAs, and the like. A "mobile device," as used herein, is not necessarily limited to devices that are conveniently portable, but may also include personal computers (PCs) or other similar computing machines. As referred to herein, a "mobile device" is equipped with, at least, one or more processors, as is generally known in the art, and an image acquisition unit (e.g., camera) allowing for a user to capture a photograph of a given subject. Further, a "mobile device" is preferably equipped with communication components, either wired or wireless, allowing for the device to communicate with external devices via a communication network. Similarly, the terms "mobile device application," "mobile application," or "application," as used herein, refer to a computer program executable by a processor installed in a "mobile device," as is generally known in the art.

It is also understood that the term "patient" or other similar term as used herein is inclusive of any subject—human or animal—on which an ocular assessment could be performed. The term "user" as used herein is inclusive of any entity capable of interacting with or controlling a mobile device. The "user" may also be the "patient," or the "user" and "patient" may be separate entities, as described herein.

Additionally, it is understood that one or more of the below methods, or aspects thereof, may be executed by at least one processor. The processor may be implemented in a mobile device, as described herein. A memory configured to store program instructions may also be implemented in the mobile device, in which case the processor is specifically programmed to execute the stored program instructions to perform one or more processes, which are described further below. Moreover, it is understood that the below methods may be executed by a mobile device comprising the processor, in conjunction with one or more additional components, as described in detail below.

Furthermore, the methods, or aspects thereof, of the present disclosure may be embodied as non-transitory computer readable media on a computer readable medium containing executable program instructions executed by the processor. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Referring now to embodiments of the present disclosure, measuring dark adaptation in patients' eyes is a procedure that can help many adults in the United States and internationally because various changes or alterations in dark adaptation characteristics can be used as early indicators of potential retinal disorders. Thus, many adults would benefit from regular dark adaptation screenings but currently forgo such beneficial care because the current screening requires expensive equipment, prolonged examinations, and costly fees.

To this end, techniques are disclosed herein relating to a mobile device application for measuring dark adaptation. Various mobile applications disclosed herein can measure dark adaptation based on basic interactions between a patient and equipment, such as equipment on the mobile phone like the display, the camera, and/or the flash. Instead of using an expensive and complicated dark adaptometer machine, such as the AdaptDx Dx-04 commonly used now, the approaches disclosed herein measure dark adaptation quickly and effectively by using a variety of different methods. Many of the methods and protocols disclosed herein follow a basic series of steps, such as first optionally bleaching an eye of a patient to be tested by exposing the eye to light. Visual stimuli with progressively lower light intensities are then presented to the test eye using a display of a mobile device, as detailed below. The patient response to the presented stimulus is recorded whenever the presented stimulus is perceived by the patient. The methods continue to show a series of stimuli of appropriate brightness and record responses of the patient until enough data has been collected such that dark adaptation can then be measured on the mobile device. Using these dark adaptation measurement protocols can thus serve as cost-effective screening and home-based monitoring tools that are accessible to a large number of at-risk individuals. The methods and protocols discussed herein can also be performed using one or more mobile devices along with additional external equipment.

Figure 2:
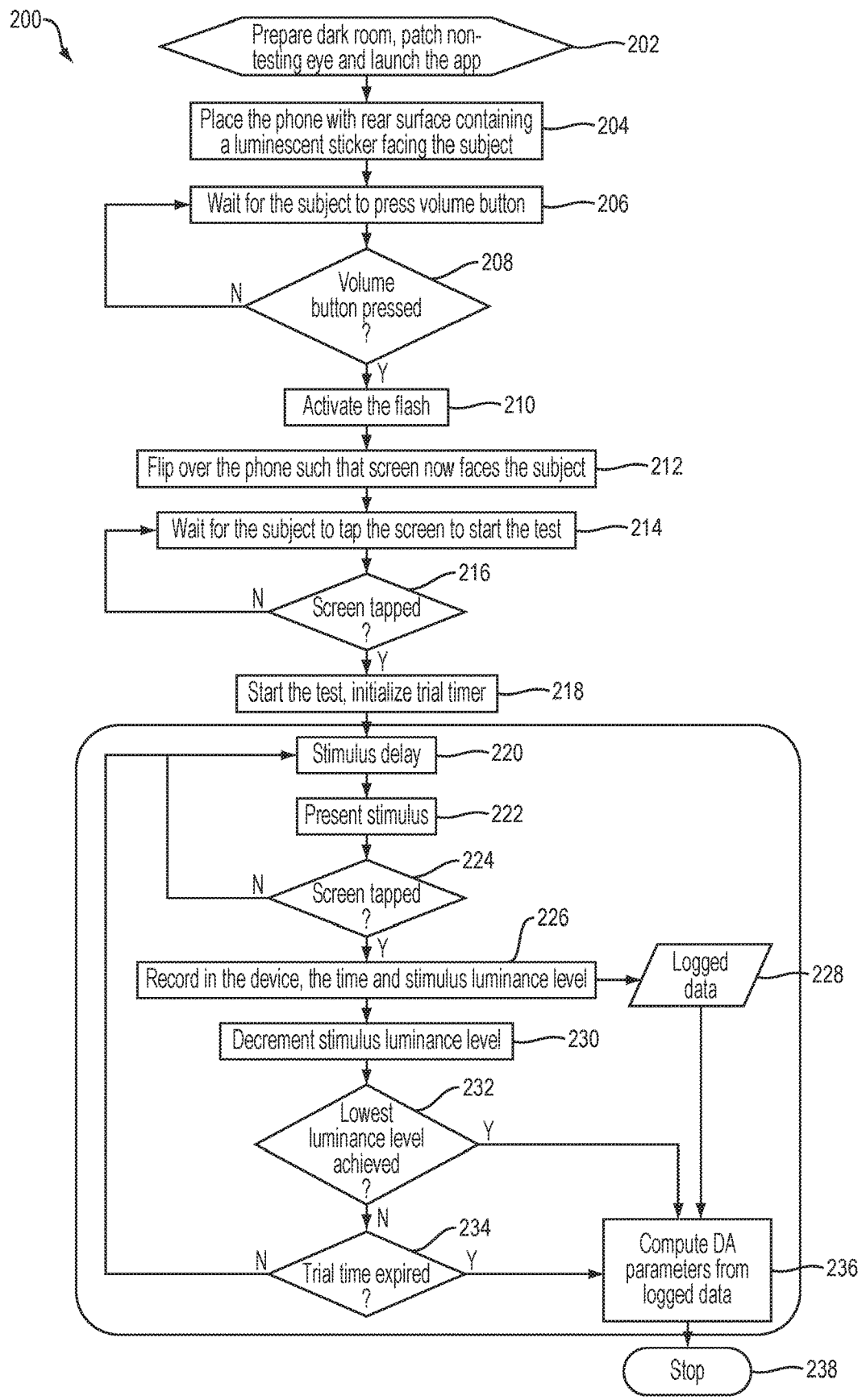
FIG. 2 illustrates one embodiment of a procedure for measuring dark adaptation using a mobile device application described herein.

For example, FIG. 1 illustrates an example diagrammatic view of a mobile device architecture according to embodiments of the present disclosure. As shown in FIG. 2, a mobile device 102 may contain multiple components, including, but not limited to, a processor (e.g., central processing unit (CPU) 110, a memory 120, a wireless communication unit 130, an input unit 140, and an output unit 150. The architecture depicted in FIG. 2 is simplified and provided merely for demonstration purposes. In view of the wide variety of commercially available mobile devices, the architecture of the mobile device 102, which is referenced throughout the present disclosure, can be modified in any suitable manner as would be understood by a person having ordinary skill in the art, in accordance with the present claims. The mobile device architecture depicted in FIG. 2 should be treated as exemplary only and should not be treated as limiting the scope of the present disclosure.

Components of the mobile device 102 will be briefly described hereinbelow, though a detailed description thereof is well known in the art and thus will be omitted from the present disclosure. The processor 110 is capable of controlling operation of the mobile device 102. More specifically, the processor 110 may be operable to control and interact with multiple components installed in the mobile device 102, as shown in FIG. 2. For instance, the memory 120 can store program instructions that are executable by the processor 110. The mobile application described herein may be stored in the form of program instructions in the memory 120 for execution by the processor 110. The wireless communication unit 130 can allow the mobile device 102 to transmit data to and receive data from one or more external devices via a communication network. The input unit 140 can enable the mobile device 102 to receive input of various types, such as audio/visual input, user input, data input, and the like. To this end, the input unit 140 may be composed of multiple input devices for accepting input of various types, including, for instance, a camera 142 (i.e., an "image acquisition unit"), touch panel 144, microphone, one or more buttons or switches, a gyroscope 146, and so forth. The input devices included in the input 140 may be manipulated by a user. For instance, a user can capture a photograph using the camera 142 by pressing the touch panel 144 in a recognized manner (i.e., a manner recognized by the processor 110). The camera 142 may include a front-facing camera and/or a rear-facing camera. Notably, the term "image acquisition unit," as used herein, may refer to the camera 142, but is not limited thereto. For instance, the "image acquisition unit" may refer to a program that acquires an image of a patient stored locally in the memory 120 or remotely on a server. The output unit 150 can display information on the display screen 152 for a user to view. The display screen 152 can also be configured to accept one or more inputs, such as a user tapping or pressing the screen 152, through a variety of mechanisms known in the art. The output unit 150 may further include a flash producing device 154 (i.e., "flash") which is a light source capable of producing a beam of light. The flash(es) can be a variety of types of light source known in the art, such as LED lights, halogens, flash bulbs, etc. The flash producing device 154 can be configured to produce a flash of light during acquisition of an image by the camera 142. One or more flashes can be incorporated on the front or back of the mobile device 102, for example a flash on the back of the device 102 for taking pictures from the rear-facing camera and/or a flash on the front of the device 102 for taking front-facing pictures.

The mobile device 102 can thus be programmed in a manner allowing it to perform the techniques for dark adaptation measurement described hereinbelow. A variety of protocols will be discussed herein that can be implemented to measure dark adaptation, but a person skilled in the art will appreciate that individual parts and/or entire protocols can be combined, rearranged, restructured, etc. and still fall within the scope of the disclosure herein.

Figure 3:
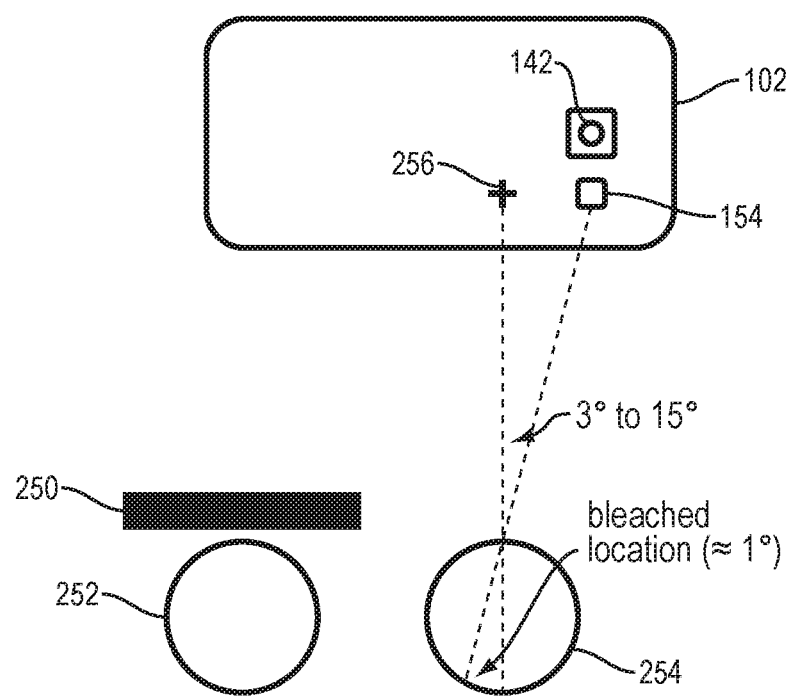
FIG. 3 illustrates an example view of the mobile device of FIG. 2 during measurement of dark adaptation.

FIG. 2 illustrates a flowchart of an exemplary embodiment 200 of a protocol for measuring dark adaptation in one or both of a patient's eyes using a mobile device, such as the device 102 and accompanying components such as input unit 140, the processor 110, the output unit 150, and the memory 120 discussed above. A user, such as the patient or a third party, can prepare a room in step 202 for dark adaptation measurement by darkening a room and placing an eye patch 250 or other cover over the eye 252 of the patient that is not being measured. The mobile application can then be launched on the mobile device 102. Relevant subject matter can be input on the application, as needed. The patient or another user can place the mobile device 102 on a surface with the rear surface of the mobile device 102 facing the patient. The mobile device 102 can be placed at a distance away from the eye 254 of the patient to be tested such that the patient can still see and read information displayed on the mobile device 102, such as approximately at reading distance (40 cm away from the patient's eye to be tested) at step 204. As illustrated in FIG. 3, a visual target 256, such as a luminescent sticker, can be fixed onto the rear surface of the mobile device 102 facing the patient, either at the time of the measurement or beforehand. The luminescent sticker can be positioned on the mobile device 102 such that an angle between a first perpendicular line of sight from the eye to be tested 254 to the visual target 256 and a second line of sight between the eye to be tested 254 and the flash 154 is approximately 3 to 15 degrees, such as 3, 4, 5, 6, 7, 8, 9, 10, 11, 12, 13, 14, or 15 degrees. The luminescent sticker, which can be visible in dark, serves as a visual fixation target for the patient's eye to be tested 254. The application can wait for input from a user at step 206. While looking at the luminescent sticker, the patient presses an input device on the mobile device 102 at step 208, such as a volume button, to activate a light source, such as the flash 154. The flash 154 is activated at step 210 for a preset duration with a preset luminance and is configured to bleach a retinal location on the eye to be tested that is peripheral to the fovea, as illustrated in FIG. 3. While a variety of placements can be used, the mobile device 102 in FIG. 3 is placed about 40 cm away from the patient such that the flash 154 bleaches 1 degree region 3 degree nasal to the fovea. Depending upon the location of the visual target 256, the eccentricity of the bleached region with respect to the fovea can be changed (for example, it can be increased possibly up to 15 degrees in the periphery). Because the patient was looking at the luminescent sticker when the flash 154 illuminates to bleach the retina, the flash 154 is able to thus bleach a predictable location of the retina.

Figure 4:
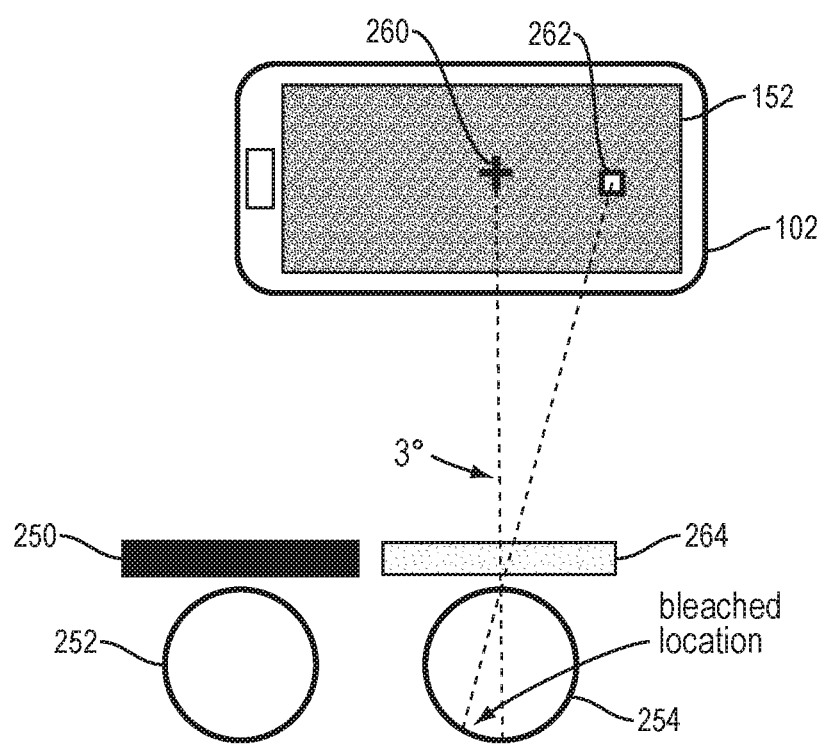
FIG. 4 illustrates an example view of the mobile device of FIG. 2 during measurement of dark adaptation.

The mobile device 102 can then be turned over so that the display screen 152 faces the patient at step 212. A timer for the dark adaptation measurements can start as the mobile device 102 is rotated or turned over after bleaching of the retina or upon actuation by the patient tapping the screen 152 or otherwise indicating that the patient is ready to proceed with the measuring process at steps 214, 216, and 218. A fixation target 260, such as a red fixation cross, of a preset luminance can be displayed on the display screen 152 after a fixed delay at steps 220 and 222. The patient focuses on the fixation target 260 on the screen 152, similar to the visual target 256, and a test stimulus 262, such as a blue stimulus, is then displayed on the screen 152 at a position relative to the fixation target 260 that approximately corresponds to the positioning of the flash 154 and the visual target 256 in the previous step. For example, in FIG. 4 a red fixation target and a blue test stimulus can be displayed on the screen 152 that are at the same relative eccentricity as the flash and the rear visual target in FIG. 3. Thus, the test stimulus can be placed to correspond to the bleached retinal region during the remaining of the test. The fixation target can have various luminance values in various tests, but the fixation target 260 can have a constant, preset luminance value during each test, for example between about 0.005 Cd/m² (candela per square meter is a unit of luminance) to 0.015 Cd/m², such as about 0.007, 0.008, 0.009, 0.010, 0.011, etc. Cd/m². The test stimulus 262 can have a range of luminance that can change throughout each test, such as log 2.0 Cd/m², and a range of sizes, such as 0.5 degrees. The patient waits until his or her eye adjusts such that the patient can see the stimulus 262, and the patient responds to being able to see the stimulus 262 by using one or more inputs, such as by tapping the display screen 152 at any location on the screen, at step 224. A tap or input by the patient can be recognized as a response that the patient can see the presented stimulus 262. While a tap on the screen 152 is generally discussed herein, a variety of inputs can be used, such as voice commands, remotes, third party inputs, various triggers, etc. A luminance of the stimulus 262 and an accumulated time from a start of the process is recorded in the mobile device 102 as the patient taps the display screen 152 at step 226, and the data can be recorded in the mobile device 102, such as in the memory 120, or on an external device in step 228. A stimulus 262 can then be displayed by the screen 152 with a slightly lower luminance than the previously displayed one at step 226. However, the same luminance level for each stimulus is maintained until the stimulus becomes visible to the patient and the patient acknowledges being able to see the stimulus 262. Thus the patient should be able to eventually see each stimulus 262 if the eye of the patient has enough time to react to the darkened conditions and the relatively low level of illumination of each stimulus. Stimuli of decreasing luminance levels continue to be shown to the patient, and the patient continues to indicate that he or she can see each stimulus, until the measurement process is terminated based on either reaching the lowest stimulus luminance (which can be a preset value or configured at the start of the test) at step 232 or a maximum allowable time for the test has expired (which can be preset or configurable at the start of the test) at step 234.

The recorded data, such as the time until acknowledgement and the luminance level of each stimulus 262, is analyzed within the mobile device 102, such as by the processor 110, using one or more developed algorithms to determine clinically-significant dark adaptation characteristic parameters for the tested eye at step 236. The test can be stopped at step 238, or if the patient wishes to test the second, untested eye, the patient can then wait for at least 10 minutes (e.g. about 10, 11, 12, 13, 14, 15, etc. minutes) in a well-lit area before testing the second eye. Additionally, the patient can optionally wear a neutral density (ND) filter 264, such as gray tinted sunglasses, during the measurement process to measure and test sensitivities that are lower than those achievable with the arrangement shown in FIGS. 3 and 4. This addition can be useful if more detailed measurements of rod-mediated dark adaptation characteristics are desired.

As discussed above, however, a variety of different procedures, protocols, test, methods, processes, etc. can be followed as described herein to successfully measure dark adaptation.

Figure 5:
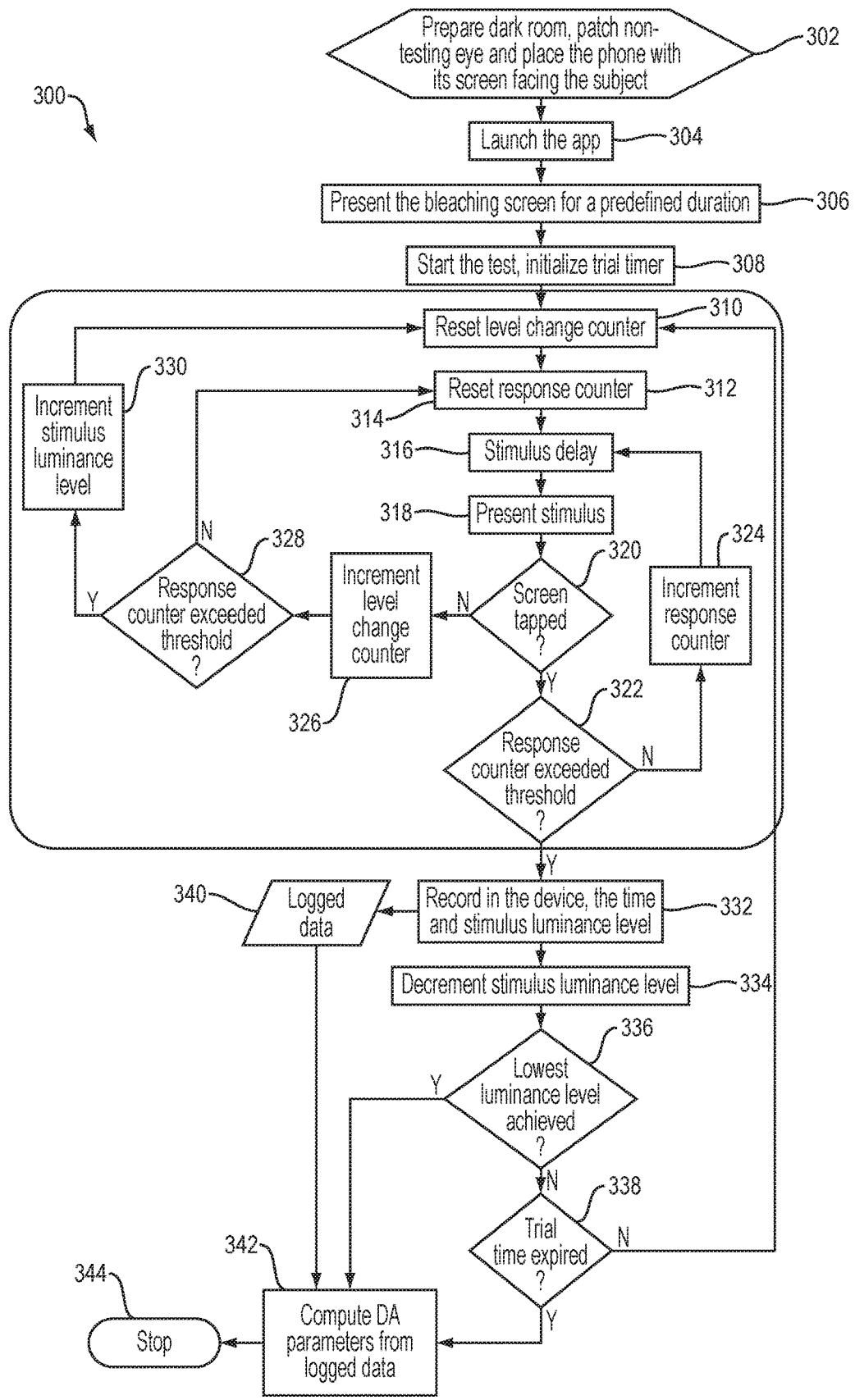
FIG. 5 illustrates another embodiment of a procedure for measuring dark adaptation using a mobile device application described herein.
Figure 6:
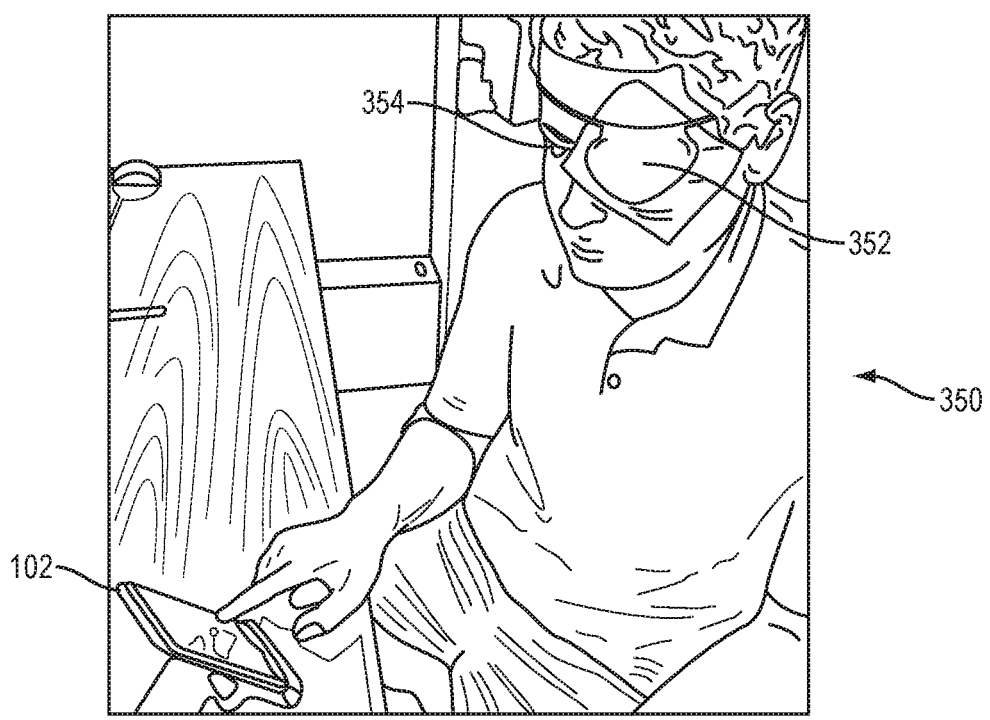
FIG. 6 illustrates a patient using the procedure of FIG. 5.

For example, FIG. 5 illustrates a flowchart of another exemplary embodiment 300 of a protocol for measuring dark adaptation similar to the embodiment 200 in one or both of a patient's eyes using a mobile device, such as the device 102 and accompanying components such as input unit 140, the processor 110, the output unit 150, and the memory 120 discussed above. A user, such as the patient 350 or a third party, can prepare a room in step 302 for dark adaptation measurement by darkening a room and placing an eye patch 352 or other cover over the eye of the patient 350 that is not being measured. The mobile application can then be launched on the mobile device 102. Relevant subject matter can optionally be input on the application, as needed. The patient 350 or another user can place the mobile device 102 on a surface with the screen 152 of the mobile device 102 facing the patient 350. As illustrated in FIG. 6, the mobile device 102 can be placed at a distance away from the eye 354 of the patient to be tested such that the patient 350 can still see and read information displayed on the mobile device 102, such as approximately at reading distance (40 cm away from the patient's eye to be tested).

The device 102 can actuate the screen 152 to show a white mobile screen with a high brightness level for a predetermined duration such as approximately 90 seconds at step 304, effectively bleaching the retina of the eye 354 to be tested while simplifying the testing process for the patient 350. The bleaching can be actuated by the patient pressing an input device on the mobile device 102, such as the screen 152, or by a variety of other mechanisms, such as other inputs, movement of the phone, launching of the mobile application, etc. In other embodiments, the screen 152 can also show one or more small moving targets during the bleaching process. The patient can be instructed to stare at the bright screen for a relatively prolonged time (for example, about 2 minutes or more, such as between about 2 minutes to about 10 minutes). During this time, the patient can stare at the moving target(s) to make the bleaching process more engaging for the patient and thus can increase compliance. Additionally, the patient can be asked by the mobile application to tap on the one or more moving targets on the screen 152. For example, one or more targets can disappear from the screen 152 after being tapped by the patient, and more targets can appear. This process can keep the patient engaged and increase compliance while the retinal location will still be bleached, similar to the bleaching achieved through use of a plain, white screen. Additionally in still other examples, the data gathered during this interaction with the patient, such as timing of screen taps, accuracy of screen taps, etc. can provide additional information for the measurement of visual acuity.

A timer for the dark adaptation measurements can start as the mobile device 102 begins to run the mobile application or by the patient otherwise indicating that he is ready to proceed with the measuring process at steps 308. A level change counter and a response counter can be reset, and a stimulus can be delayed in steps 310, 312, and 316, and as further discussed below. A test stimulus similar to the test stimulus 262 is then displayed on the screen 152 at a position. A fixation target similar to the target 260 can optionally be displayed, as well, with a fixed luminance. The test stimulus can have a range of luminance values that can change throughout the test, similar to the stimulus 262 above.

The patient 350 waits until his eye adjusts such that the patient can see the stimulus, and the patient responds to being able to see the stimulus by using one or more inputs, such as by tapping the display screen 152 at any location on the screen, at step 320. As illustrated in FIG. 5, if a response counter exceeds a threshold value after the patient 350 taps the screen 152 at step 322, the test proceeds similar to the embodiment 200 discussed above. However, the embodiment can also incorporate additional steps. For example, if a response counter does not exceed a threshold value, the response counter is incremented at step 324 and the mobile application returns to the stimulus delay at step 316 to then take the patient 350 through presenting the stimulus at step 318 and tapping the screen at step 320 again. This feedback loop can optionally be used to gather additional data to make the measuring herein more accurate. Additionally or alternatively, a second feedback loop can be used if a screen tap is not detected at step 320. If no tap is detected, the mobile application can increment a level change counter at step 326 and then determine if the response counter exceeds a threshold value at step 328. If the response counter does not exceed a threshold value, the mobile application returns to step 314 and resets the response counter. If the response counter does exceed a threshold value, the mobile application will increase an increment stimulus luminance level and return to step 310 to reset the level change counter. Effectively, this feedback loop causes the patient 350 to be presented with stimuli at incrementally increasing luminance levels until the patient has successfully identified the stimuli enough times to proceed to the next portion of the protocol to gather additional data and allow for a more accurate measurement of dark adaptation. The threshold values herein can either be preset or can be set at the time of the test.

After completing the feedback loops discussed above, the patient will proceed to the remaining portion of the test if a response counter exceeds a threshold value after the patient 350 taps the screen 152 at step 322 again. A luminance of the stimulus and an accumulated time from a start of the process is recorded in the mobile device 102 as the patient taps the display screen 152 at step 332, and the data can be recorded in the mobile device 102, such as in the memory 120, or on an external device at step 340. A new stimulus can then be displayed by the screen 152 with a slightly lower luminance than the previously displayed one at step 334. Stimuli of decreasing luminance levels continue to be shown to the patient, and the patient continues to indicate that he can see each stimulus, until the measurement process is terminated based on either reaching the lowest stimulus luminance (which can be a preset value or configured at the start of the test) at step 336 or a maximum allowable time for the test has expired (which can be preset or configurable at the start of the test) at step 338. However, another optional feedback loop can return the patient and the mobile application to step 310 to reset the level change counter and can require the patient to proceed through the test again if the trial time has not expired. Similar to the other feedback loops, this optional feedback loop can be used to retest the patient to gather more data and provide a more accurate measurement of dark adaptation.

The recorded data, such as the time until acknowledgement and the luminance level of each stimulus, is analyzed within the mobile device 102, such as by the processor 110, using one or more developed algorithms to determine clinically-significant dark adaptation characteristic parameters for the tested eye at step 342. The test can be stopped at step 344, or if the patient wishes to test the second, untested eye, the patient can then wait for at least 30 minutes in a well-lit area before testing the second eye.

Measuring dark adaptation can also be performed using one or more additional pieces of equipment in other embodiments. For example, FIG. 7 illustrates a flowchart of another exemplary embodiment 400 of a protocol for measuring dark adaptation similar to the embodiment 200 in one or both of a patient's eyes using a mobile device, such as the device 102 and accompanying components such as input unit 140, the processor 110, the output unit 150, and the memory 120 discussed above.

However, the patient 450 can also use specialized goggles or headsets, such as a set of virtual reality goggles or VR goggles 452 in FIG. 8A with an exemplary mobile device such as the Galaxy S7 having specifications as illustrated in FIG. 8B and an exemplary mobile application illustrated in FIG. 8C. While the overall measuring process can be similar to that of embodiments 200, 300, the use of goggles or headsets, such as the VR goggles 452, can simplify the process by allowing a patient to more easily test one eye. While a Galaxy S7 is illustrated, any mobile device can be used, such as a mobile device that has communication capabilities (such as the ability to make a phone call), a touchscreen interface, Internet or general connectivity access, and an operating system capable of running applications.

In some embodiments, the use of goggles or headsets can also allow for some modifications to the steps, for example by allowing the patient to test both eyes at once while still providing independent measurement of each eye through dichoptic viewing. Dichoptic viewing allows a separate and independent field to be viewed by each eye such that a first stimulus can be presented to a left eye of the patient and a second, different stimulus can be presented to a right eye, allowing for dual eye measurements to be performed. Dual eye measurement can refer to independent dark adaptation measurement of each eye, similar to the approaches discussed above, but performed simultaneously on each of the patient's right and left eyes with alternating stimulus presented on each eye. The ability to perform dual eye measurement allows for much faster measurement than measuring one eye at a time, which can involve a patient setting up any measurement component(s) (such as any of those discussed above) for a first measured eye, patching or covering a second non-measured eye, measuring the first eye, and then switching everything around to test the second eye. By using a dual eye measurement mode or mechanism, the measurements can be performed much faster while avoiding or simplifying several of the steps required for measuring individual eyes one at a time. However, to perform independent yet dual or simultaneous measurements on both eyes of the patient, dual eye measurement mechanisms use various approaches to visually separate or isolate each of the patient's first and second eyes relative to each other and/or relative to any external testing environment. For example, various goggles or headsets such as the VR goggles 452 can separate the patient's eyes by using screens, padding, extra material, sealing features around each eye, etc. to create a physical barrier between the eyes relative to each other and/or a physical barrier between each eye and any external testing environment that may introduce external visual stimulation and/or light as each eye is measured individually (while again allowing both measurements on each individual eye to be carried out at the same time similar to the steps discussed above). Simultaneous testing of both eyes can be carried out by alternatively displaying various visual stimulations to each eye in turn such that testing is conducted during a defined testing period that does not involve re-adjusting any testing equipment, removing any goggles or headsets, patching or un-patching any eyes, allowing a patient to stop testing and/or remove any components serving to isolate or separate each eye, etc. until measurements are achieved for both eyes of the patient. Alternatively displaying various visual stimulations to each eye in turn can include either measuring a first eye entirely and then measuring a second eye or displaying various initial stimulations to each eye and switching back and forth between eyes before displaying various second stimulations, third stimulations, etc. and switching back and forth between each eye each time before proceeding to the various second stimulations, third stimulations, etc.

Figure 7:
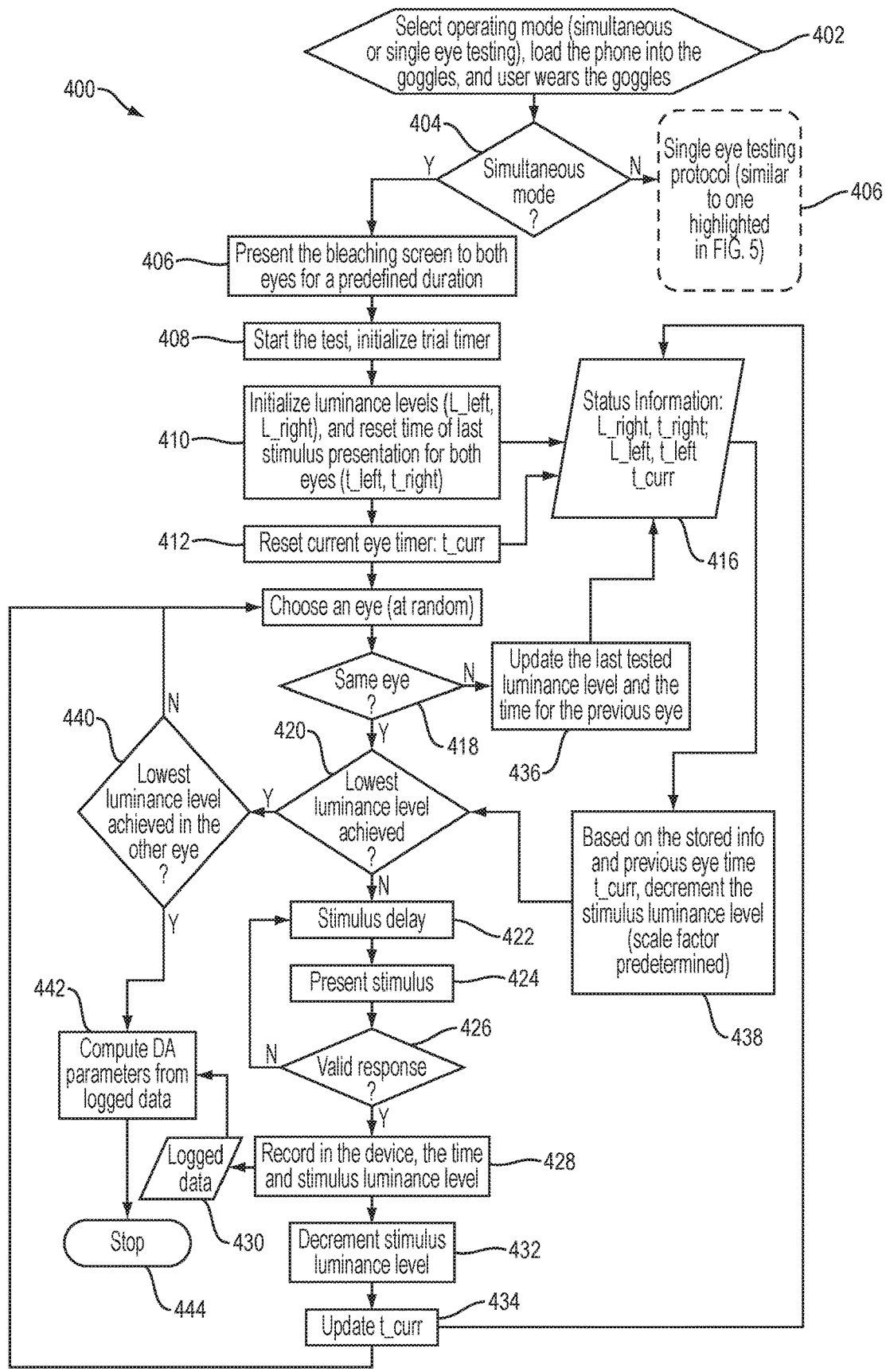
FIG. 7 illustrates another embodiment of a procedure for measuring dark adaptation using a mobile device application described herein.

In the illustrated embodiment in FIGS. 7 and 8, a user, such as the patient 450 or a third party, can open the mobile application and select an operating mode on the mobile application, such as simultaneous eye testing or single eye testing, at step 402. As illustrated, single eye testing is still possible using goggles or headsets. The goggles or headsets simply can also provide simultaneous or dual testing mechanisms in part because they can separate each eye. Relevant subject matter can optionally be input on the application, as needed. The user can load the mobile device 102 into the VR goggles 452 and can place the VR goggles 452 onto the patient 450. If a single eye testing mode is selected at step 404, the test can proceed similar to the test provided above in embodiment 300 in step 406. If simultaneous eye testing mode is selected at step 404, the device 102 can actuate the screen 152 to show a white mobile screen with a high brightness level for a predetermined duration, such as between approximately 60 seconds to 120 seconds (e.g. 60, 70, 80, 90, 100, 110, 120, etc. seconds) or approximately 90 seconds, at step 406, effectively bleaching the retinas of both eyes. The bleaching can be actuated by the patient pressing an input device connected to the mobile device 102, such as a Bluetooth remote 454, or by a variety of other mechanisms, such as other inputs, movement of the phone, voice activation, etc.

A timer for the dark adaptation measurements can start as the mobile device 102 begins to run the mobile application or by the patient otherwise indicating that he is ready to proceed with the measuring process at step 408. Luminance levels L_left, L_right for the left and right eyes are initialized, and times t_left, t_right of the last stimulus presentation for the left and right eyes are reset at step 410, similar to the various reset steps in embodiment 300 discussed above. The current eye timer t_curr is reset at step 412, and an eye is chosen at random to perform measurements on in step 414. Status information can also be updated and stored at step 416 after steps 410 or 412. The mobile application then determines if the same eye is being examined as a previous loop in step 418. If the answer is yes, the mobile application will determine if the lowest luminance level has been achieved for the eye in question at step 420. At this point, the stored status information and previous eye time t_curr can be used to decrease stimulus luminance level based on a scaled factor that is predetermined at step 438. If the lowest luminance level has not been achieved, a stimulus delay will run at step 422, a stimulus will be presented to the patient at step 424, and the patient will indicate when the stimulus is perceived at step 426, for example by using the Bluetooth remote 454. This basic process is similar to the test steps discussed above in embodiments 200, 300. If the patient indicates a perceived stimulus and the response is correct, the time taken by the patient and stimulus level of the stimulus will be recorded at step 428 (either to the mobile device 102 or a remove device). The data will be logged at step 430 and the stimulus luminance level will be decreased at step 432. The current time t_curr will be updated at step 434, and the data will be stored as the status information (as performed in step 416). The mobile application will also proceed back to step 414 to choose an eye at random and run through the measuring steps again for an individual eye.

At step 418, if the same eye is not being tested, the last tested luminance level and the time for the previously tested eye will be updated at step 436, and the data will be stored as the status information (as performed in step 416). The stimulus step will then be decreased (as performed in step 438), and the mobile application will proceed to step 420 to determine if the lowest luminance level has been achieved.

At step 420, if the lowest luminance level has been achieved, the mobile application determines if the lowest luminance level has been achieved in the other eye at step 440. If the answer is no, the mobile application returns to step 414 to choose an eye at random and run through the measuring steps again for an individual eye.

At step 440, if the lowest luminance level has been achieved in the other eye, the recorded data, such as the time until acknowledgement and the luminance level of each stimulus that was logged during step 430, is analyzed within the mobile device 102, such as by the processor 110, using one or more developed algorithms to determine clinically-significant dark adaptation characteristic parameters for both eyes at step 442. The test can be stopped at step 444 after measurements have been determined for both eyes.

While all of the embodiments discussed above provide useful measurements, the use of the VR goggles 454 can provide additional control over the testing area. For example, there can be more control ensuring that the viewing distance is constant and maintained at a set, predefined distance and consequently, the peripheral eccentricity of the stimulus on the retina can be more tightly maintained so that there is more precision on the location of the retina that is being tested). Additionally, this approach does not need to be performed in a darkened room as the VR goggles naturally provide a dark viewing environment, VR googles systems for most mobile devices (such as smartphones) are dichoptic (meaning both eyes can see the screen independently). As such, both the eyes can be tested in a single session instead of having to wait to test the second eye. To generate even more accurate measurements, a stimulus is provided to one of the patient's eyes at a time, and the patient is asked to indicate when the stimulus is visible by pressing different buttons on the remote or input device that correspond to the right or left eye. Thus the measurement process can be must faster while still providing accurate results.

Through the processor and camera on the mobile device 102 and the mobile application, a user, such as a third party, can also indirectly monitor the eye movements of the patient by using a technique of blind spot monitoring, discussed in greater detail below in embodiment 500, where once every few trials a bright stimulus (such as a stimulus brighter than the current test stimulus, for example between about 10 percent and about 500 percent brighter, such as 10 percent, 20 percent, 30 percent, 40 percent, 50 percent, 60 percent, 70 percent, 80 percent, 90 percent, 100 percent, etc. brighter) is presented in the blind spot and the patient's response is noted. The frequency with which the patient perceives the stimulus presented in the blind spot indicates the fixation stability during the test, again resulting in additional data that can result in increased accuracy in measuring the dark adaptation. The precise calibration of the blind spot location for the patient in such a situation can be done prior to the measurement process by presenting a glowing dot at a location on the screen that corresponds approximately with the blind spot (for example, about 10 to 15 degrees temporal to the eye) and allowing the subject to move the dot until it appears using the remote. Using VR goggles 454 also allows a user to test different locations at varying eccentric points around the fovea (similar to a perimetry instrument).

Figure 9:
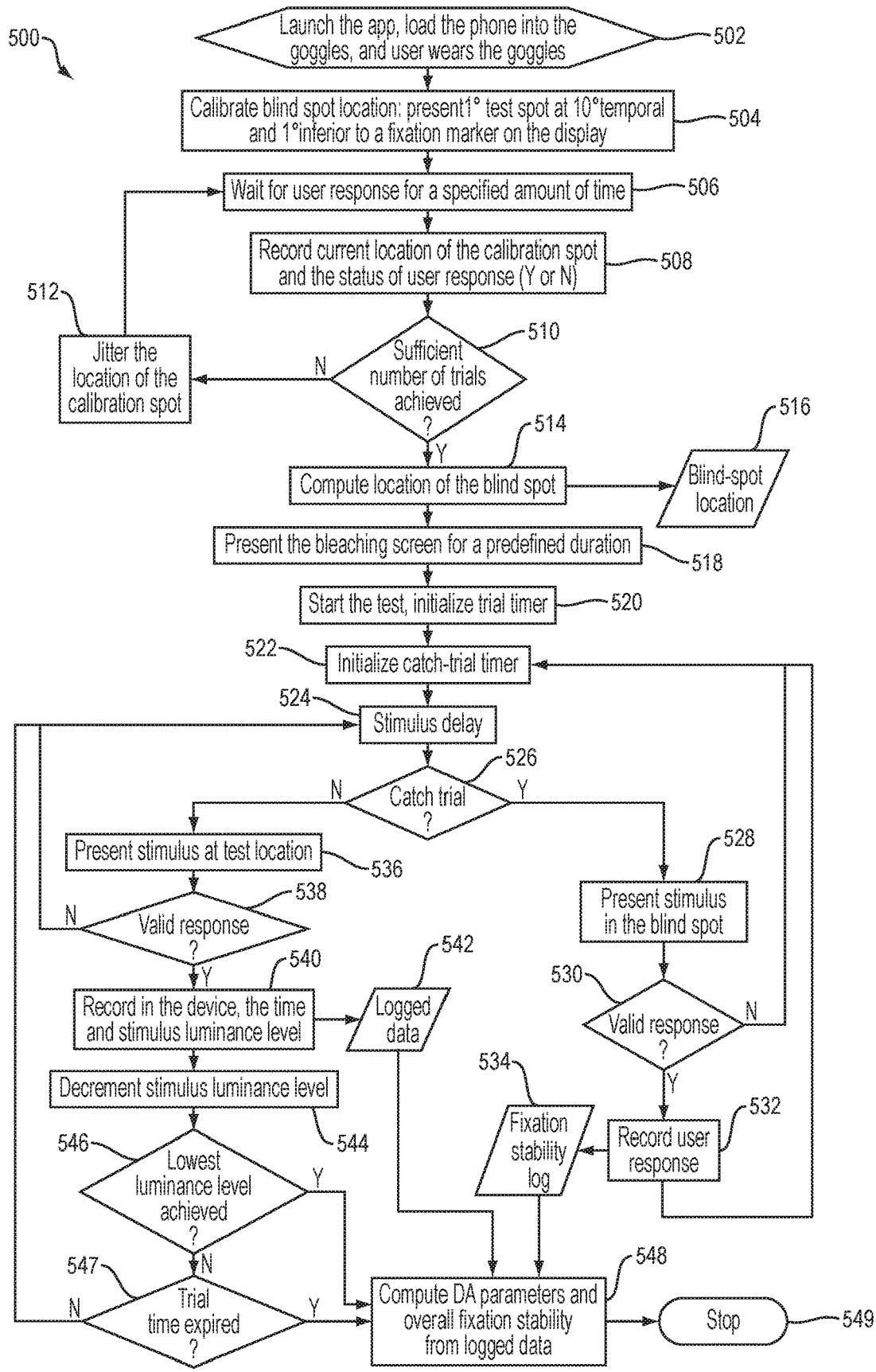
FIG. 9 illustrates another embodiment of a procedure for measuring dark adaptation using a mobile device application described herein.
Figure 10:
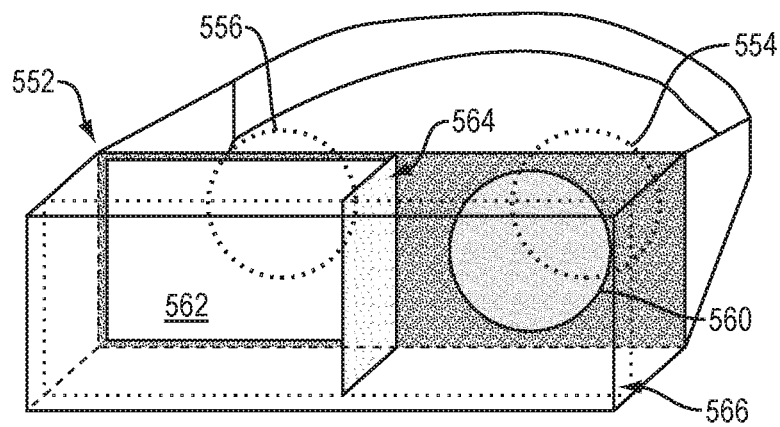
FIG. 10 illustrates an embodiment of goggles that can be used with the procedure of FIG. 9.

While the illustrated VR goggles 452 in FIG. 8A work with the mobile device 102, other embodiments of goggles or headsets can incorporate and be configured for other mobile devices, and still other embodiments can be configured such that no mobile device is received therein, as discussed below. For example, variations can be made in virtual reality goggles to provide additional benefits during measuring. For example, FIG. 9 illustrates a flowchart of another exemplary embodiment 500 of a protocol for measuring dark adaptation similar to the embodiment 200 in one or both of a patient's eyes using a mobile device, such as the device 102 and accompanying components such as input unit 140, the processor 110, the output unit 150, and the memory 120 discussed above. However, the patient can also use a set of specialized virtual reality goggles, for example the specialized goggles 552 in FIG. 10.

The specialized goggles 552 can facilitate direct monitoring of eye movements during measurement of dark adaptation. For example, the viewing lens 560 that is customarily present for both eyes is only present in one eye 554 (the eye being tested) while an opening 562 is formed in front of the second eye 556 that is not being tested so that the screen 152 of the mobile device 102 can be seen directly. While the patient will not be able to focus on the screen 152 through the opening using the eye 556 not being tested, a front-facing camera of the mobile device 102 can view the eye 556 directly and capture videos of the eye 556 of the patient while the patient is wearing the specialized goggles 552. An opaque screen 564 can be positioned between the two eyes 554, 556 so that the tested eye 554 is able to remain in relative darkness, and a slot 556 can be formed in a front portion of the goggles 552 to receive the mobile device 102 therein. Therefore, using the specialized goggles 552, movement of the non-tested eye 556 can be monitored by the front-facing camera as the tested eye 554 is being measured for dark adaptation. This information can allow a user to determine a variety of different factors. For example, because both eyes tend to move together simultaneously, it will enable objective measurement of a fixation stability during the actual measurement process of the tested eye 554 and help to determine whether the stimulus is being seen precisely by the retinal location being tested. The non-tested eye 556 being monitored by the camera can be presented with a bright screen on the portion of the screen 152 that is viewable from the opening 562 to aid the front camera to focus while the test is run on the remaining screen for the tested eye 554.

In use, a user, such as the patient or a third party, can open the mobile application, and relevant subject matter can optionally be input on the application, as needed. The user can load the mobile device 102 into the specialized goggles 552 and can place the goggles 552 onto the patient in step 502. When the goggles 552 are in place, the blind spot location can then be calibrated in step 504 by presenting a 1 degree test spot at 10 degrees temporal and 1 degree inferior to a fixation target or marker that is shown on the display screen 152 and similar to the fixation target 260 discussed above. The application can then wait for a specified amount of time for the patient to respond to indicate that the spot has been seen in step 506. The mobile application can then record the current location of the calibration spot and the status of the patient's response in step 508, and the mobile application can then determine if a sufficient number of trials have been achieved in step 510. If not enough trials have been achieved, the location of the calibration spot can be jittered or moved in step 512, and the mobile application can return to step 506 to wait for another patient response to increase the accuracy and correct positioning of the blind spot location calibration. Once enough trials have been achieved to accurately locate the blind spot, the processor 110 can compute the location of the blind spot in step 514. The blind spot location is stored on the device 102 in step 516. The bleaching screen is then presented to the eye 554 to be measured at step 518 for a predefined duration, such as 90 seconds, effectively bleaching the retina. The bleaching can be actuated by the patient pressing an input device connected to the mobile device 102, such as a Bluetooth remote or by a variety of other mechanisms, such as other inputs, movement of the phone, voice activation, etc.

A timer for the dark adaptation measurements can start as the mobile device 102 begins to run the test or by the patient otherwise indicating that he is ready to proceed with the measuring process at step 520. A catch-trial timer can be initialized at step 522 that can be used with the blind spot calibration to determine fixation stability, as discussed above. Next, a stimulus delay can occur at step 524, and the processor 110 can determine if there should be a catch trial for the fixation stability at step 526.

If there should be a catch trial, the screen 152 can present a stimulus in the blind spot at step 528. If the response from the patient on the blind spot stimulation is valid, the response can be recorded in step 532 and the data can be recorded in the fixation stability log in step 534. If not, the process can return to step 522 and the catch-trial timer can be initialized.

If no catch trial is needed in step 526, a stimulus can be presented at the test location at step 536 and a fixation target can be displayed on the screen 152, similar to the fixation target 260 and the test stimulus 262. If there is not a valid response from the patient in response to the stimulus at step 538, the process can return to the stimulus delay in step 524. If there is a valid response, the time taken by the patient and the stimulus luminance level of the stimulus will be recorded at step 540 (either to the mobile device 102 or a remove device). The data will be logged at step 542 and the stimulus luminance level will be decreased at step 544.

The process is continued until either the lowest luminance level is achieved in step 546 or the total allowable time of the trial has expired in step 547, at which point the recorded data, such as the time until acknowledgement and the luminance level of each stimulus that was logged, is analyzed within the mobile device 102, such as by the processor 110, using one or more developed algorithms to determine clinically-significant dark adaptation characteristic parameters for the tested eye 554 at step 548. The test can be stopped at step 549.

Figure 11:
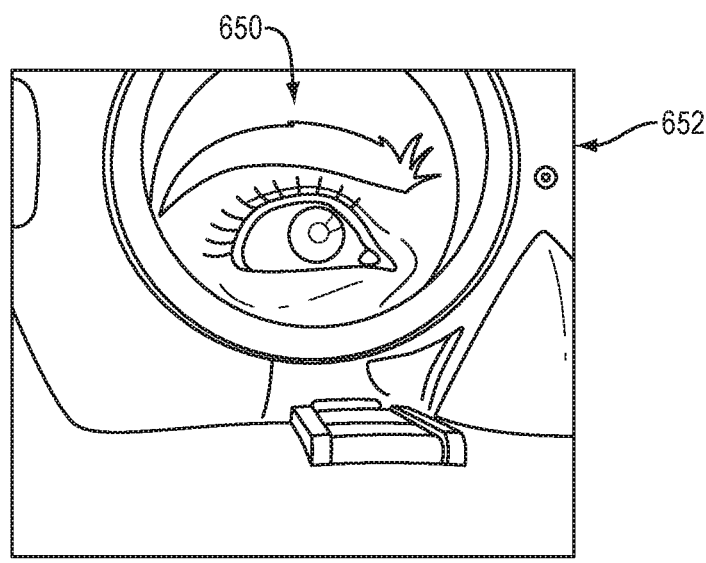
FIG. 11 illustrates a patient using the procedure of FIG. 9.
Figure 12:
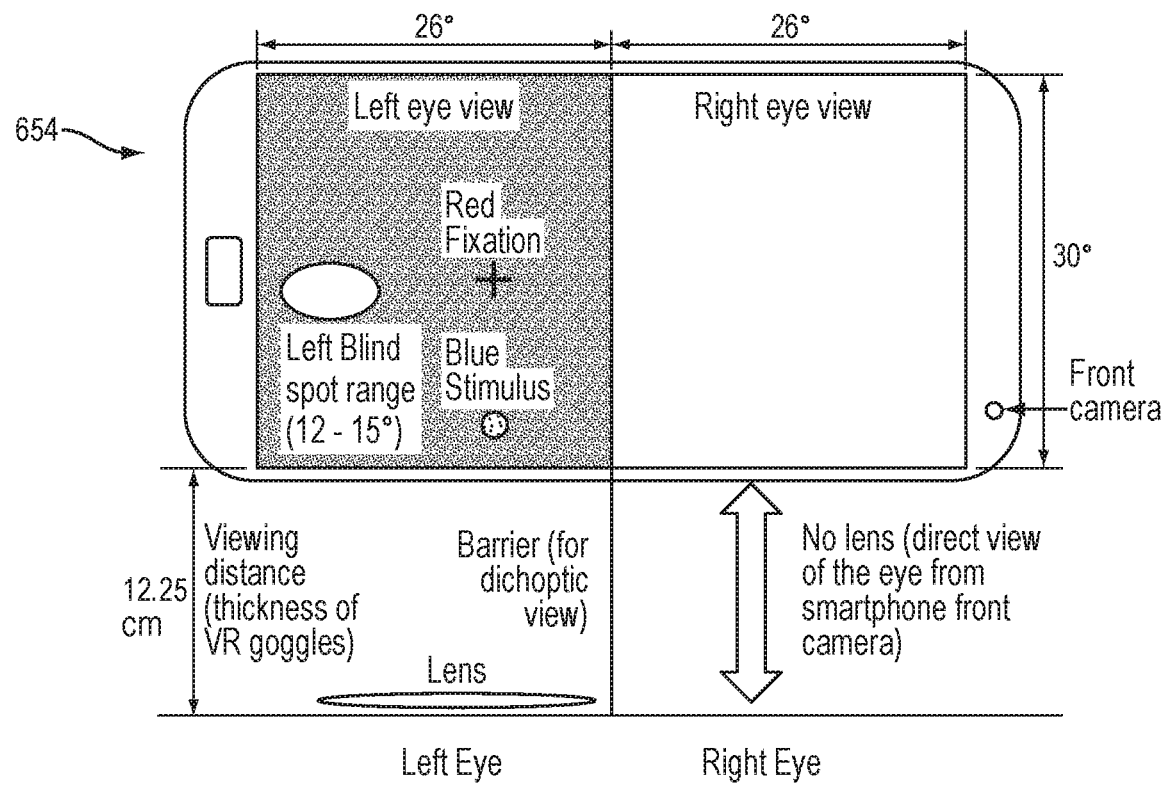
FIG. 12 illustrates an example view of the mobile device of FIG. 9 during measurement of dark adaptation.

FIGS. 11 and 12 illustrate an exemplary set-up for the present embodiment. FIG. 11 illustrates an exemplary image of the non-tested eye of a patient 650, for example the right eye, obtained from the front-facing camera of a smartphone 654 through a clear eye piece of an embodiment of the specialized goggles 652 disclosed herein with the lens removed and the non-tested eye illuminated by a white screen on the smartphone. In other embodiments, the area occluded by the frames of the specialized googles illustrated in FIG. 11 may not be present. FIG. 12 illustrates a screenshot of an embodiment of the mobile application that can be used when using the specialized goggles. A white screen is projected on approximately half of the display screen of the smartphone and displayed to the non-tested eye through the cleared out eye piece of the specialized goggles, which illuminates the right, non-tested eye and aids in monitoring the right eye using a front-facing camera. The left, tested eye is presented with the mobile application on approximately half of the display screen of the smartphone because the eye piece has an appropriate lens, which means the display screen will be in focus. The barrier between the eyes blocks out the light from the while screen on half of the display screen and preserves a dark environment for the left, tested eye.

As discussed above, eye movement of a patient can be tracked during dark adaptation measurement through use of the front-facing camera of a mobile device, such as the mobile device 102. Fixation of the tested eye can be monitored via automated processing of images of the non-tested. For example, fixation monitoring of the tested eye can be performed by using the specialized goggles 652 by determining the eye movement trace from one or more images or videos captured through the front-facing camera of the smartphone 654 illustrated above by imaging the non-tested eye of the patient 650. In some examples, fixation can be enforced or required by monitoring eye movement and providing one or more alerts, notifications, etc. to the patient if fixation is incorrect. Additionally and/or alternatively, the data collected by fixation monitoring can be used by the mobile application to correct or enhance dark adaptation measurements.

The goggles or headsets do not have to incorporate a mobile device therein at all. For example, various dedicated VR goggles can be used that are separate from mobile phone VR goggles. Dedicated VR goggles can be used that are configured primarily to provide VR experiences without using a mobile phone that communicate with, connect with, or are configured to engage with a variety of computer systems beyond a mobile device. For example, VR goggles can be used that incorporate various additional features or mechanism therein, such as built-in eye-tracking capabilities. The systems and methods of dark adaptation measurements discussed herein can be incorporated into such VR goggles and can potentially utilize the additional features and capabilities provided thereon. For example, one or more VR goggles dedicated to or focused primarily on gaming, or playing video games, can be incorporated herein and used to perform dark adaptation measurements. Various similar algorithms, methods, steps, etc. can exist between dark adaptation measurement on mobile device VR goggles and dark adaptation measurement on dedicated VR goggles, and any of the steps, approaches, components, etc. discussed above can be applied to dedicated VR goggles. Such dedicated VR goggles can operate with various associated computer systems, such as a variety of different gaming consoles (for example, any versions of Sony PlayStation(s), Microsoft Xbox(es), Nintendo Switch(es), etc.), a mobile device as discussed above, a tablet computer, a desktop computer, any device with a processor and a memory, a remote server (e.g. various cloud computing server banks), various laptop computers, etc. Alternatively, various dedicated VR goggles can incorporate one or more functionalities and components therein such that the dedicated VR goggles can operate independently of any external computer system and can perform all functionalities directly thereon. For example, FIG. 13 illustrates dedicated VR goggles 700 in communication with an associated computer system 702 that can be similar to any of the computer system discussed above and can either be an external system connected through wires or wirelessly with the dedicated VR goggles 700 or can be incorporated therein.

Test Data:

An overview of the testing data will first be discussed, and a detailed discussion will follow below. As the testing data shows, dark adaptation measurements can be taken to detect retinal diseases. The mobile application disclosed herein was developed to measure dark adaptation and perform a preliminary evaluation in normal vision (NV) and visually impaired subjects. Testing was done for one eye (with the other eye patched) by placing an exemplary Samsung Galaxy S8 smartphone in front of the patient sitting in a dark room (40 cm from the test eye). Bleaching was performed with a bright smartphone screen (luminance ≈300 Cd/m$^2$). However, a range of luminance is possible, such as between about 100 Cd/m$^2$ to about 400 Cd/m$^2$. A series of blue stimuli of size 1.5 degree between luminance range of −1.15 to −4.33 log Cd/m$^2$ were presented 8 degrees inferior to the fixation on the smartphone display. However, again, a range of values can be used, such as stimuli of size 0.5 degree to 2.5 degree between luminance range of −0.15 to −5.33 log Cd/m$^2$. The patient tapped the screen whenever the stimulus was visible, and the time and stimulus threshold were logged. Test duration was capped at 20 minutes. First, the mobile application vas evaluated by examining the effect of age on DA characteristics in NV subjects (n=15), between 22 to 82 years of age (mean 45, std. 20) with visual acuity (VA) 20/25 or better, and without diagnosis of any vitreo-retinal conditions. Then, one patient was tested with retinal damage due to myopic degeneration (MRD) (VA 20/100, age 62) and one patient with optic nerve atrophy (ONA) (VA: 20/500, age 40) to verify whether the effect of pathology can be detected by the app. Finally, DA characteristics were measured in 4 early and intermediate stage AMD patients and were compared with 10 age-matched NV subjects above 50 years of age. Outcome measures were time to rod-cone-break ($t_{RCB}$), time to reach the minimum test threshold luminance, $t_{term}$, and the area under the time-luminance threshold curve (AUC). AUC was normalized using the preset bounds on test duration and luminance thresholds of the device. Regression analysis was used for determining age effect on outcome measures. Non-parametric Wilcoxson rank sum test was used to compare the outcomes between NV and AMD patients. The results indicated that $t_{RCB}$, $t_{term}$, and AUC increased with age in NV subjects ($t_{RCB}$: $R^2$=0.47, p=0.003; $t_{term}$: $R^2$=0.34, p=0.013; AUC: $R^2$=0.41, p=0.006). The coefficients of repeatability for $t_{RCB}$, $t_{term}$, and AUC were ±2.1 min, ±5.4 min, and ±4.4%, respectively. DA was greatly prolonged in the MRD subject with the final luminance threshold 1.2 log Cd/m$^2$ higher than the minimum test threshold at the termination of the test. The AUC was outside the 95% CI of regression of age and 52% greater than the NV mean. On the other hand, for the ONA subject, $t_{term}$ (12.8 min) was not significantly different than the NV subjects (within the interquartile range of the regression of age), and the AUC was 21% larger than the NV mean, but still within the 95% CI of regression of age. The age distribution was not significantly different in AMD and elderly NV subjects (avg. age NV=63, AMD=66, p=0.57). The AUC was significantly larger for AMD subjects compared to the NV (p=0.033). In conclusion, the mobile application is able to detect the effects of age and retinal pathology on DA characteristics.

Figure 13:
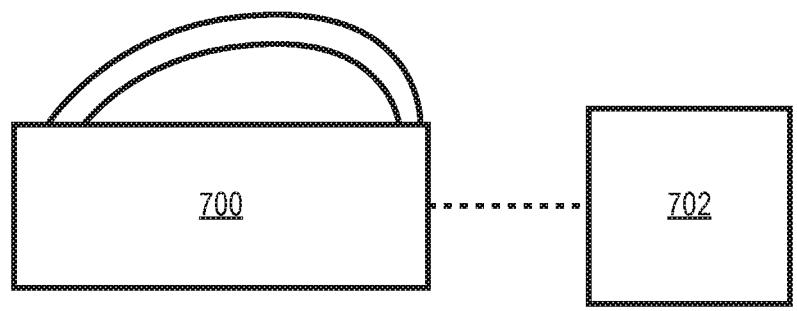
FIG. 13 illustrates another embodiment of VR goggles with an associated computer system.
Figure 14:
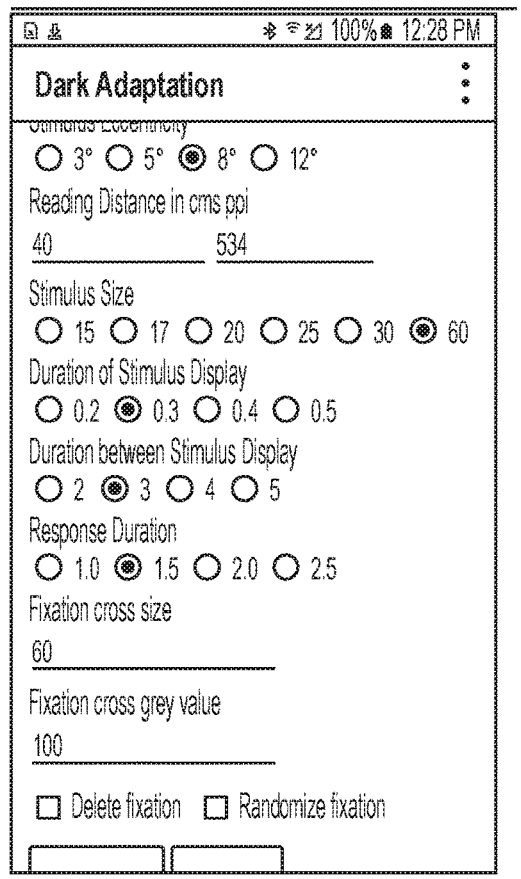
FIG. 14 illustrates a screenshot of an embodiment of the mobile application disclosed herein.
Figure 15:
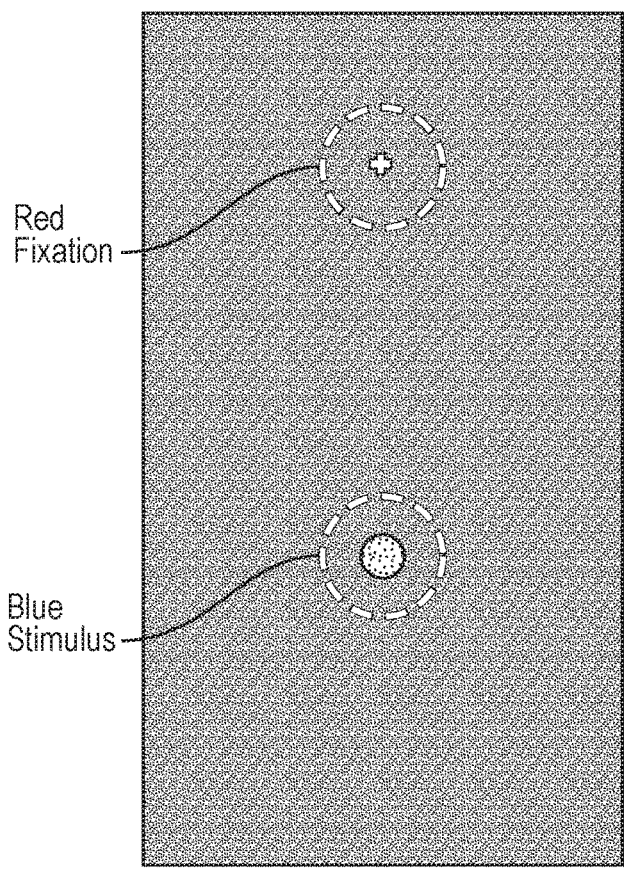
FIG. 15 illustrates a screenshot of the mobile application of FIG. 14 in use.

The detailed results of various tests using the processes discussed herein are illustrated in FIGS. 13-22. For example, FIGS. 13 and 14 show screenshots of an embodiment of the mobile application discussed herein for measuring dark adaptation. The illustrated embodiment allows for setting of various test parameters such as stimulus size, duration of stimulus display, response duration, and various other parameters. While this ability is useful in some settings, such as in a clinic or lab testing, some embodiments may have various parameters hardcoded to make it easier for patients to operate. FIG. 14 thus shows a screenshot of one embodiment of a configuration screen that allows setting of different parameters related to stimuli and fixation targets, and FIG.

15 illustrates a screenshot of one embodiment of a test screen that shows a red fixation cross and a blue stimulus that appears for a fraction of a second. The patient then taps the screen whenever the blue dot becomes visible. The time for the response (from the beginning of the test) is recorded for the presented stimulus and a new stimulus with lower luminance is then presented at the same location. The log of the recorded responses can then be processed to compute the clinically relevant dark adaptation parameters provided below.

For tests presented herein, dark adaptation measurement methods are computed on a Samsung Galaxy S8 smartphone, however any mobile device can be used. Some of the test results related to the stimulus and fixation marker appearances are shared or common between all methods (between using the VR goggles and not using them). When using VR goggles with mobile devices, both eyes of a patient can be able to see half a screen in the horizontal direction and a full vertical range in both the eyes. For the exemplary mobile device used herein, the Samsung Galaxy S8, half of the screen can a horizontal angle of approximately 20 to 30 degrees, and more preferably approximately 26 degrees, which is sufficient for blind spot monitoring in each eye. Also dichoptic viewing (common for VR goggles) allows both eye to be tested in the same session (with alternating stimulus presented on each eye as discussed in detail above).

Figure 16:
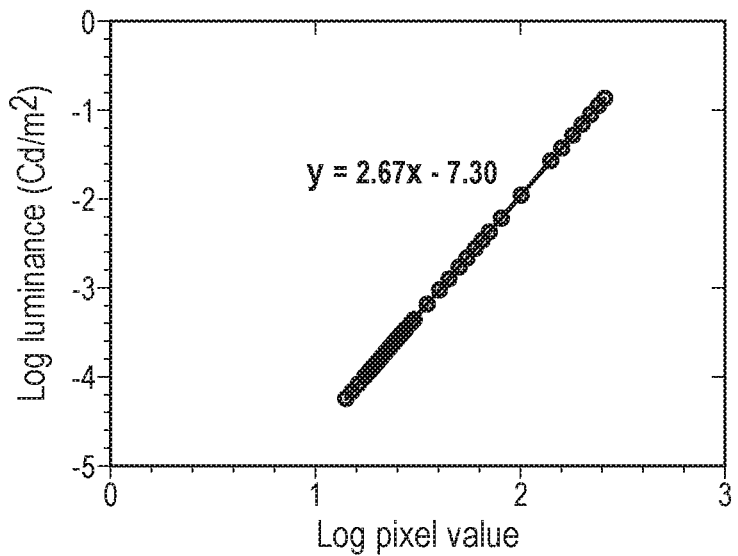
FIG. 16 illustrates a graph of screen luminance of a Samsung Galaxy S8 used as an exemplary mobile device herein.

To determine if commercial mobile device screens had sufficient luminance dynamic range for dark adaptation measurements, display of the Samsung Galaxy S8 was characterized with USB2000 spectrometer (OceanOptics). The resulting luminance for different pixel values (about 255 to 13, however other values are possible such as 0 to 255, etc.) for blue color channel is shown in FIG. 16 for minimum screen brightness settings. A lookup table was created in the software for pixel value—luminance relationship. Then a gamma function was fit to the data. While pixel values below 13 were visible to dark adapted normal eyes, they were below the measurement limit of the spectrometer and hence not shown here. The luminance decreased linearly with decreasing pixel values and the minimum luminance level that was measured was $4.64 \times 10^{-5}$ $Cd/m^2$. Some mobile devices can display luminance levels that are below the known cone threshold in humans (z between −3 to −3.5 log $Cd/m^2$). Thus, a part of the rod component of the DA characteristics can be measured using a mobile device, as provided herein. Based on the measurements, the overall luminance range of the exemplary Samsung Galaxy S8 smartphone was ≈$10^6$ $Cd/m^2$, with a maximum of ≈300 $Cd/m^2$ at maximum brightness setting with white screen. At the lower pixel values (below 7), human subjects could not see the stimuli even after 30 minutes of dark adaptation. The dynamic range of the smartphone display was determined to be sufficient as it was possible to elicit valid responses in mesopic and scotopic ranges.

Figure 17:
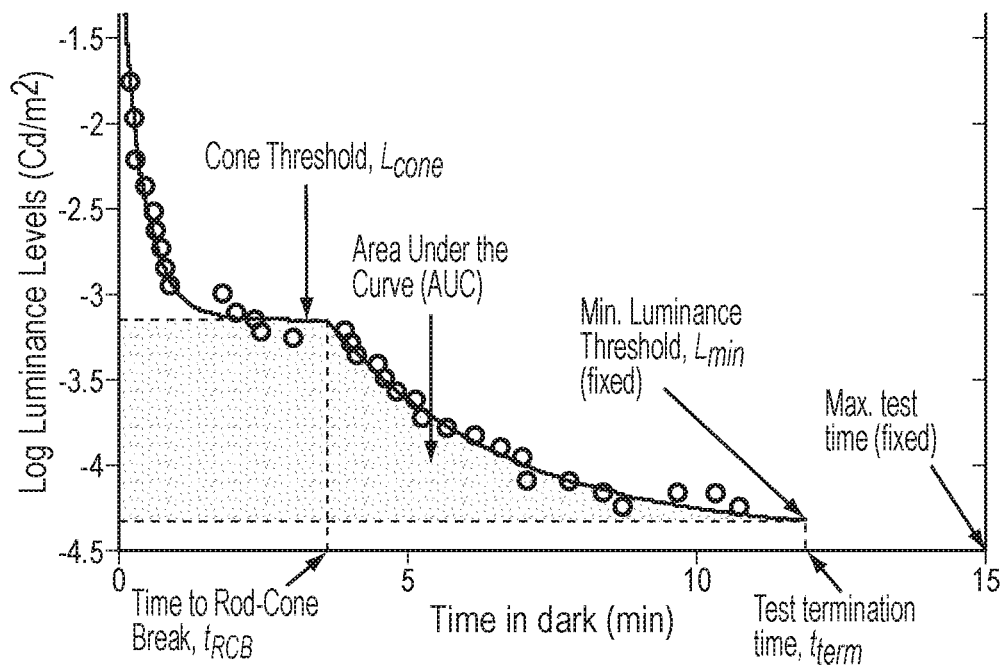
FIG. 17 illustrates graphs of dark adaptation characteristics of a normally sighted subject measured using a measurement process disclosed herein.

FIG. 17 shows the dark adaptation characteristics obtained from a normally sighted male individual (age 36) using a testing process similar to the embodiment 300 discussed above without dilating the eyes. The characteristics resemble to the line diagram of typical dark adaptation characteristics found in the art. Based on the characteristics obtained from this process, the clinically relevant dark adaptation parameters of rod-cone break, cone threshold, and time to reach minimum luminance threshold can be estimated. Additionally, the area under the dark adaptation curve can also be computed. It can be seen that cone threshold for all the subjects is close to −3 log $Cd/m^2$, which is considered to be the approximate luminance level at which the cones saturate in normally sighted humans. Also, a rod-cone break time of about 5 to 7 minutes is typical, but depending on the pre-adapting light level and the measurement conditions, it can vary. Overall, the characteristics shown in FIG. 17 can thus be considered as the expected characteristics for normally sighted individuals. While various models have been proposed for fitting functions to the DA characteristics, customized software algorithms have been developed to automatically estimate clinically relevant dark adaptation parameters: time to rod-cone break, cone threshold, time to reach device baseline threshold, and rod-recovery rate. Additionally, the area under the dark adaptation curve can be used as an outcome measure.

Figure 18:
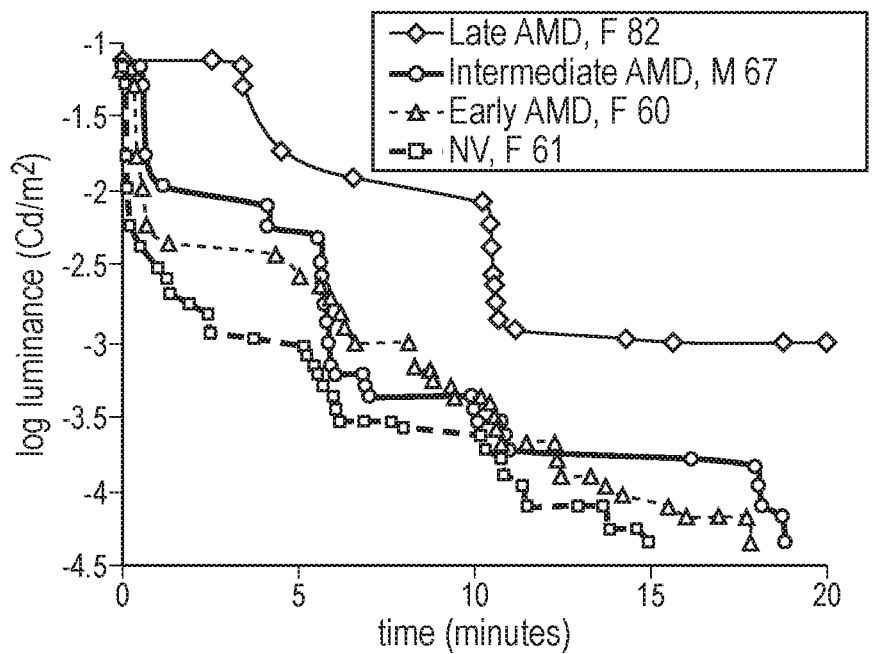
FIG. 18 illustrates graphs of dark adaptation characteristics of a normally sighted and 3 AMD patients (early, intermediate, and late stage AMD) measured using a measurement process disclosed herein.

FIG. 18 shows the dark adaptation characteristics obtained from for an early, an intermediate, and a late stage AMD patient and an elderly subject without AMD (normal control, NV) using a testing process similar to the embodiment 300 discussed above without dilating the eyes. Visual Acuity (VA) in the test eye was: NV & early AMD—20/20, intermediate AMD—20/30, and late AMD—20/60. Qualitative differences in the dark adaptation curves are observed for 1 elderly NV subject and 3 AMD patients of varying severity. The late AMD patient has elevated photoreceptor threshold at the end of the allotted test time. Slight delays are seen for early and intermediate AMD patients compared to the NV subject.

Figure 19:
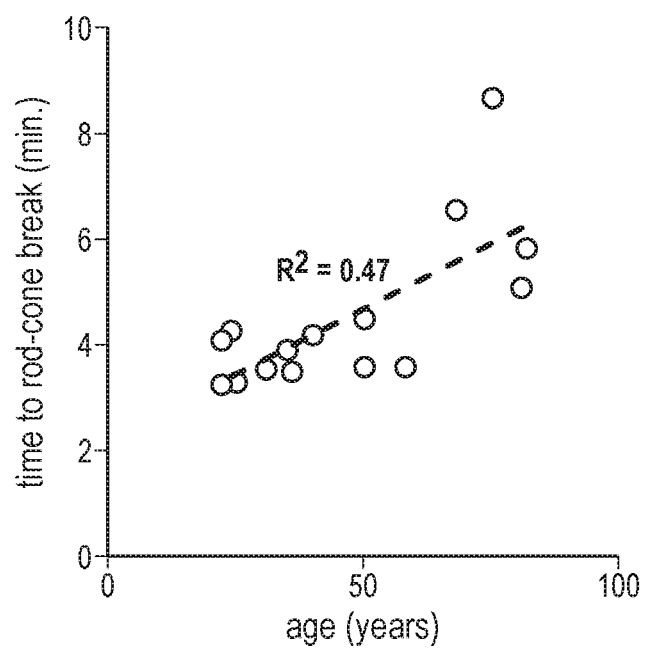
FIG. 19 illustrates a graph of time to rod-cone break for subjects using a measurement process disclosed herein.
Figure 20:
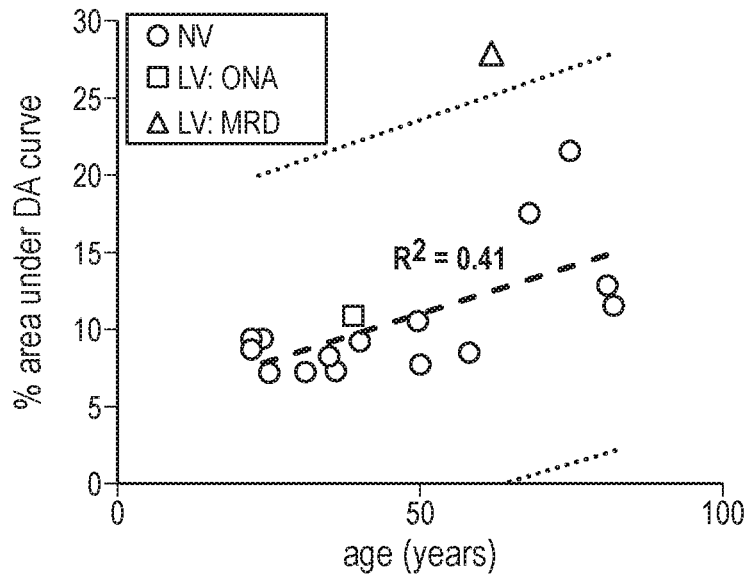
FIG. 20 illustrates a graph of area under the curve of dark adaptation characteristics for subjects using a measurement process disclosed herein.

The mobile application discussed herein was also tested using a Samsung Galaxy S8 on 15 normally sighted subjects of ages between 22 to 82 without diagnosis of any retinal damage. However, the subjects can have a variety of age ranges, such as between about 15 years to about 100 years, 40 years to 90 years, 50 years to 85 years, etc. One 62 year old subject was also tested with retinal damage due to myopic degeneration and one 39 year old low vision subject with optic nerve atrophy (no known retinal damage). Furthermore, 4 early and intermediate stage AMD patients were also tested. The goals of these studies were; i) to show that an effect of age on dark adaptation, which is expected to happen as natural part of aging, is indeed seen in the dark adaptation measurements with the mobile application discussed herein,—ii) dark adaptation characteristics in the subject with damaged retina are different than characteristics of a low vision subject without damaged retina, and iii) dark adaptation characteristics are significantly different (delayed) in AMD subjects compared to age-matched NV, with the results being illustrated in FIGS. 19-21. FIG. 19 shows the plot of age vs. time to rod-cone break. The time to rod cone break increased with increasing age, showing the delays in dark adaptation with age. This is a known phenomenon, and by seeing the same effect in the measurements using the mobile application discussed herein, it can be confirm that the mobile application measurements are valid. FIG. 20 shows the plot of age vs. area under the curve. Again with age, the area under the curve increases, indicating that older subjects take longer to reach the minimum device threshold and are more likely to not complete the test in the stipulated time (area is a combination of the threshold reached and the time required). The data for the two low vision subjects are overlaid. The time to complete the test and the area under the curve for the subject without retinal damage was statistically similar as that for age-matched normally sighted subjects. The subject with retinal damage recorded the largest area under the curve. The delay in dark adaptation due to retinal damage is relatively well known. Therefore, these results show that that the same effect can be obtained when using the mobile application discussed herein. This indicates that the mobile application measurements are valid.

Figure 21:
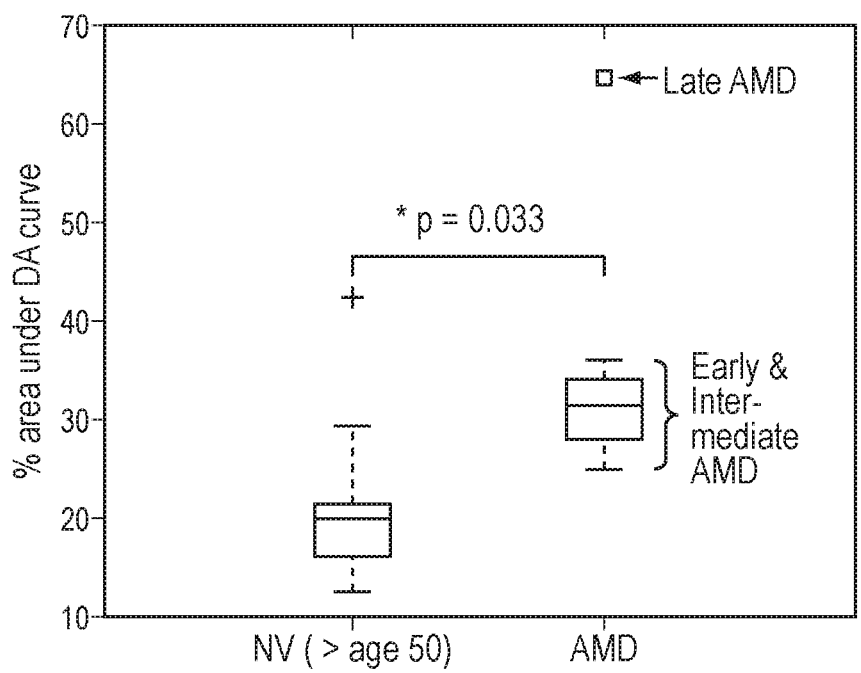
FIG. 21 illustrates a graph of area under the curve of dark adaptation characteristics for subjects using a measurement process disclosed herein.

FIG. 21 compares measurements for the AMD patients and age-matched normal controls (NV). A large area under the dark adaptation curve value (AUC) is indicative of delays in reaching lowest luminance threshold and/or higher photoreceptor sensitivities. The % AUC values for the early and intermediate AMD subjects (n=4) were significantly larger than NV subjects (n=10) above 50 years of age (Wilcoxson, p=0.033). The AUC for late AMD subject (not included in the statistical comparison) is overlaid for demonstration. The difference in the ages for NV and AMD groups was not significant (avg. NV=63, AMD=66; Wilcoxson p=0.57).

Figure 22:
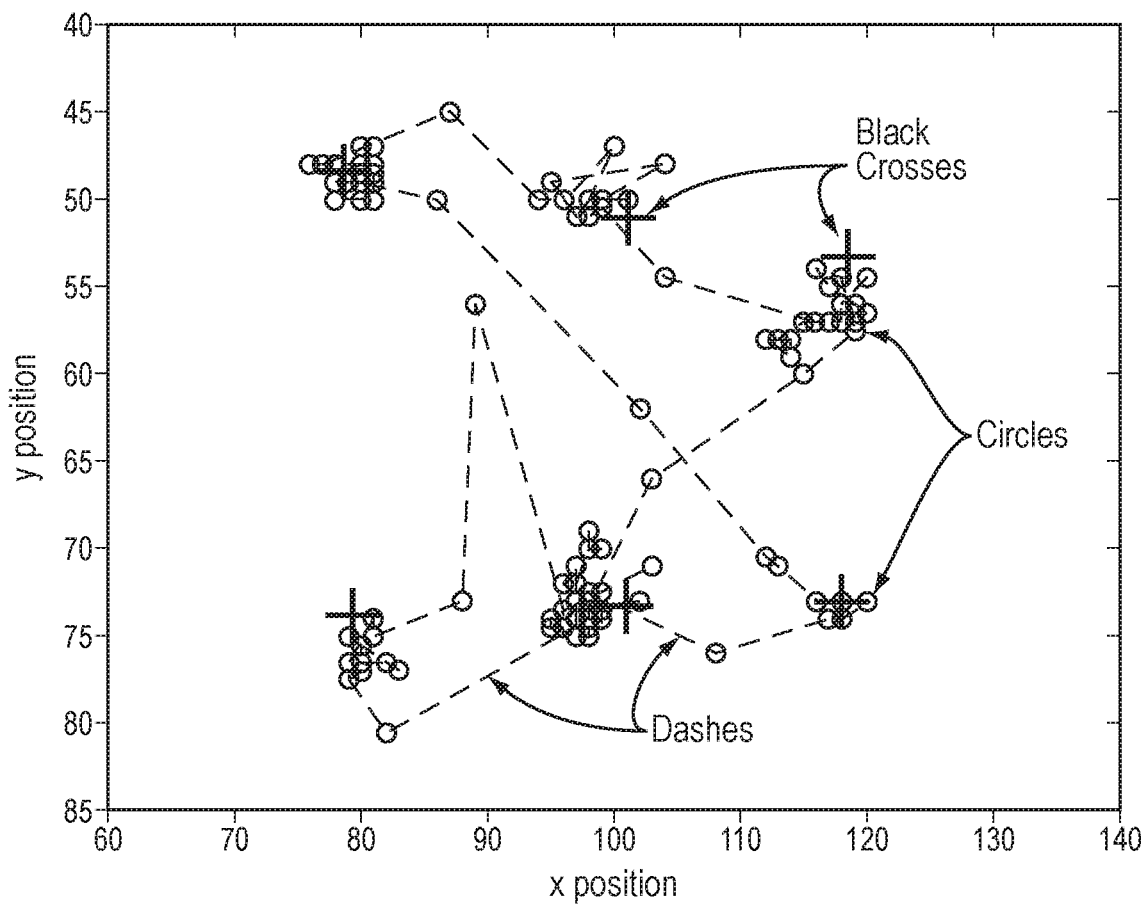
FIG. 22 illustrates a graph of test data demonstrating the feasibility of fixation monitoring.

FIG. 22 illustrates test data demonstrating the feasibility of fixation monitoring using specialized goggles similar to the specialized goggles 652 described above. The figure illustrates eye movement trace from video captured through the front-facing camera of a mobile device similar to the smartphone 654 when inside the specialized goggles. The test-eye made 6 fixations, which were ground truth locations that are illustrated as black crosses. Each red circle in the figure shows the eye position in a video frame. Fixations, shown by clusters of red points around each black cross, and the eye position during saccade, shown by circles on trajectories connecting the black crosses, can be seen in the detected pattern. The results thus show the feasibility of fixation monitoring while performing DA testing.

Thus the processes discussed herein can provide clinically meaningful dark adaptation parameters, eye dilation not required which speeds up and simplifies the measurements, the measurements have short durations (for example, between about 5 to 25 minutes, between about 10 to 15 minutes, etc.), the measurements are easy to perform and administer, and the measurements are repeatable within subjects. Because various degenerative eye disorders, such as AMD, can go undetected for years in some cases, there is a need for a method that can identify these risks early in elderly population. In order to be largely accessible to the general population and to be effective as an easy to use test for the detection of various disorders like AMD, the dark adaptation measurement process needs to be simplified without affecting the quality and clinical relevance of the information that is gathered. Thus the dark adaptation measurements provided herein, such as those performed using various mobile devices and/or equipment provided here, can serve as screening tools that are accessible to a large number of at-risk individuals. Additionally, they can also serve as tools for home monitoring of already diagnosed patients with retinal disorders.

While there have been shown and described illustrative embodiments that provide for a mobile device application for dark adaptation measurement, it is to be understood that various other adaptations and modifications may be made within the spirit and scope of the embodiments herein. For instance, while a mobile device is frequently mentioned throughout the present disclosure, the techniques described herein may also be implemented on desktop computers or similar machines. Thus, the embodiments of the present disclosure may be modified in any suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein.

What is claimed is:

1. A method for measuring dark adaptation characteristics comprising:
    exposing at least one eye of a patient to a light source to bleach a retinal location of the at least one eye;
    placing a mobile device in a mobile device viewer and placing the mobile device viewer over first and second eyes of the patient, wherein the mobile device view has only one lens over the first eye of the patient and an open space over the second eye of the patient;
    displaying to the at least one eye on the mobile device a figure with a luminance and waiting until the patient communicates with the mobile device to acknowledge that the patient can see the figure;
    measuring and recording a level of the luminance and a time period between first displaying the figure and the patient communicating with the mobile device;
    continuing to display additional figures with decreasing luminance one at a time until the patient communicates with the mobile device to acknowledge that the patient can see each additional figure and to measure and record each decreasing luminance and each time period between first displaying each additional figure and the patient communicating with the mobile device until either a maximum allowable time period has expired or an additional figure with a lowest possible luminance has been displayed by the mobile device and acknowledged by the patient; and
    determining, by a processor, dark adaptation measurements of the at least one eye based on the measured and recorded luminance and time periods.

2. The method of claim 1, further comprising prior to exposing the eye of the patient to a light source, placing a rear surface of the mobile device facing the patient with at least one luminescent visual target thereon such that the patient can see the luminescent visual target.

3. The method of claim 1, wherein exposing the eye of the patient to the light source to bleach the retinal location of the eye includes one of actuating a flash on the mobile device or increasing brightness of a display on the mobile device.

4. The method of claim 1, further comprising placing an eye patch over an eye of the patient that is not being measured.

5. The method of claim 1, further comprising incrementing luminance of a displayed figure and waiting until the patient communicates with the mobile device to acknowledge that the patient can see the displayed figure.

6. The method of claim 1, further comprising selecting an operating mode of the mobile device from one of a single eye measurement mode and a dual eye measurement mode.

7. The method of claim 1, wherein the dual eye measurement mode includes exposing both eyes of the patient to the light source and determining, by the processor, dark adaptation measurements of both eyes of the patient based on the measured and recorded luminance and time periods.

8. The method of claim 1, further comprising placing the mobile device in virtual reality goggles.

9. The method of claim 1, wherein the mobile device is one of a mobile phone, a tablet computer, or a laptop computer.

10. A method for measuring dark adaptation characteristics of a patient using virtual reality goggles (VR goggles) comprising:

exposing at least a first eye of the patient to a light source in the VR goggles to bleach a retinal location of the first eye;

displaying to the first eye on a display of the VR goggles a first fixation target and a first test stimulus, the first fixation target having a constant luminance and the first test stimulus having a variable luminance;

instructing the patient by the VR goggles or an associated computer system to look at the first fixation target with the first eye and waiting until the patient communicates with the VR goggles or the associated computer system to acknowledge that the patient can see the first test stimulus with the first eye;

reducing the luminance of the first test stimulus on the display of the VR goggles and waiting for the patient to acknowledge that the patient can see the first test stimulus with the reduced luminance;

continuing to reduce the luminance of the first test stimulus on the display and waiting for the patient to acknowledge that the patient can see each reduced luminance first test stimulus until either a maximum allowable time period has expired or the first test stimulus with a lowest possible luminance has been displayed by the VR goggles and acknowledged by the patient;

recording in a memory of the VR goggles or the associated computer system a level of the luminance of the first test stimulus and a time period between first displaying the first test stimulus and the patient communicating with the VR goggles or the associated computer system for each instance of displaying the first test stimulus;

determining, by a processor of the VR goggles or the associated computer system, dark adaptation measurements of the first eye based on the measured and recorded luminance and time periods; and further comprising monitoring fixation of the first eye based on images taken of a second eye by an imaging device of the VR googles.

11. A method for measuring dark adaption characteristics of a patient using virtual reality goggles (VR goggles) comprising:

exposing at least a first eye of the patient to a light source in the VR goggles to bleach a retinal location of the first eye;

displaying to the first eye on a display of the VR goggles a first fixation target and a first test stimulus, the first fixation target having a constant luminance and the first test stimulus having a variable luminance;

instructing the patient by the VR goggles or an associated computer system to look at the first fixation target with the first eye and waiting until the patient communicates with the VR goggles or the associated computer system to acknowledge that the patient can see the first test stimulus with the first eye;

reducing the luminance of the first test stimulus on the display of the VR goggles and waiting for the patient to acknowledge that the patient can see the first test stimulus with the reduced luminance;

continuing to reduce the luminance of the first test stimulus on the display and waiting for the patient to acknowledge that the patient can see each reduced luminance first test stimulus until either a maximum allowable time period has expired or the first test stimulus with a lowest possible luminance has been displayed by the VR goggles and acknowledged by the patient;

recording in a memory of the VR goggles or the associated computer system a level of the luminance of the first test stimulus and a time period between first displaying the first test stimulus and the patient communicating with the VR goggles or the associated computer system for each instance of displaying the first test stimulus, determining, by a process of the VR goggles or the associated computer system, dark adaption measurements of the first eye based on the measured and recorded luminance and time periods; and further comprising exposing a second eye of the patient to the light source;

displaying to the second eye a second fixation target and a second test stimulus, the second fixation target having a constant luminance and the second test stimulus having a variable luminance;

instructing the patient by the VR goggles to look at the second fixation target with the second eye and waiting until the patient communicates with the VR goggles or the associated computer system to acknowledge that the patient can see the second test stimulus with the second eye;

reducing the luminance of the second test stimulus on the display of the VR goggles and waiting for the patient to acknowledge that the patient can see the second test stimulus with the reduced luminance;

continuing to reduce the luminance of the second test stimulus on the display and waiting for the patient to acknowledge that the patient can see each reduced luminance second test stimulus until either a maximum allowable time period has expired or the second test stimulus with a lowest possible luminance has been displayed by the VR goggles and acknowledged by the patient;

recording in a memory of the VR goggles or the associated computer system a level of the luminance of the second test stimulus and a time period between first displaying the second test stimulus and the patient communicating with the VR goggles or the associated computer system for each instance of displaying the second test stimulus;

determining, by the processor, dark adaptation measurements of each of the first and second eyes of the patient based on the measured and recorded luminance and time periods;

wherein the first and second fixation targets and the first and second test stimuluses are presented to the first and second eyes through an alternating pattern such that each of the first and second eyes are measured simultaneously; and wherein the VR goggles visually isolate the first and second eyes relative to each other during measuring.

12. The method of claim 10, wherein the VR goggles comprise dedicated VR goggles having built-in eye-tracking functionality.

13. The method of claim 10, wherein the associated computer system comprises at least one of a gaming console, a desktop computer, a device with a processor and a memory, a remote server, a mobile phone, a tablet computer, and a laptop computer.

14. A system for measuring dark adaptation characteristics of a patient comprising:

a mobile device including at least one light source, at least one input device, at least one imaging device, memory, at least one processor, and a display, the display being configured to display a fixation target and a test stimulus, the fixation target having a constant luminance and the test stimulus having a variable luminance, the processor being configured to measure luminance of the test stimulus and a time period between displaying the test stimulus and the patient acknowledging the test stimulus, the processor being configured to determine dark adaptation measurements of at least one tested eye based on the measured and recorded luminance and time periods; and a mobile device viewer configured to receive the mobile device and be placed over first and second eyes of the patient, the mobile device viewer having one lens over the first eye of the patient and an open space over the second eye of the patient.

15. The system of claim 14, wherein the at least one imaging device includes a forward- facing camera on the mobile device.

16. The system of claim 14, wherein the at least one imaging device includes a rear-facing camera on the mobile device.

17. The system of claim 14, wherein the at least one light source includes a forward-facing flash on the mobile device.

18. The system of claim 14, wherein the at least one light source includes a rear-facing flash on the mobile device.

* * * * *

UNITED STATES PATENT AND TRADEMARK OFFICE
CERTIFICATE OF CORRECTION

| | | |
|---|---|---|
| PATENT NO. | : 11,937,877 B2 | |
| APPLICATION NO. | : 16/971975 | |
| DATED | : March 26, 2024 | |
| INVENTOR(S) | : Shrinivas Pundlik et al. | |

It is certified that error appears in the above-identified patent and that said Letters Patent is hereby corrected as shown below:

In the Specification

Column 20, Line 16, "vas" should be --was--.

In the Claims

Claim 11, Column 25, Line 40, "adaption" should be --adaptation--.

Claim 11, Column 26, Line 8, "process" should be --processor--.

Claim 11, Column 26, Line 9, "adaption" should --adaptation--.

Signed and Sealed this
Eleventh Day of June, 2024

Katherine Kelly Vidal
*Director of the United States Patent and Trademark Office*